United States Patent
McNeff et al.

(10) Patent No.: US 6,846,410 B2
(45) Date of Patent: Jan. 25, 2005

(54) HIGH STABILITY POROUS METAL OXIDE SPHERULES USED FOR ONE-STEP ANTIBODY PURIFICATIONS

(75) Inventors: Clayton V. McNeff, Anoka, MN (US); Peter W. Carr, St. Paul, MN (US); Steven J. Rupp, Minnetonka, MN (US); Dwight R. Stoll, Anoka, MN (US); Danielle R. Hawker, Shakopee, MN (US); Lorinda D. Zigan, Browerville, MN (US); Kerry G. Johnson, Minneapolis, MN (US)

(73) Assignee: ZirChrom Separations, Inc., Anoka, MN (US)

(*) Notice: Subject to any disclaimer, the term of this patent is extended or adjusted under 35 U.S.C. 154(b) by 16 days.

(21) Appl. No.: 10/428,231

(22) Filed: May 2, 2003

(65) Prior Publication Data

US 2004/0007530 A1 Jan. 15, 2004

Related U.S. Application Data

(60) Provisional application No. 60/377,451, filed on May 3, 2002.

(51) Int. Cl.[7] .............................................. B01D 15/08
(52) U.S. Cl. .............................. 210/198.2; 210/502.1; 210/635; 210/656; 502/401
(58) Field of Search .................................. 210/635, 656, 210/659, 198.2, 502.1; 502/400, 401; 428/403, 404

(56) References Cited

U.S. PATENT DOCUMENTS

| | | | |
|---|---|---|---|
| RE20,957 E | * | 12/1938 | Drelich ....................... 427/331 |
| 3,782,075 A | | 1/1974 | Kirkland |
| 3,862,908 A | | 1/1975 | Fitch et al. |
| 3,892,580 A | | 7/1975 | Messing |
| 3,956,179 A | | 5/1976 | Sebestian et al. |
| 4,010,242 A | | 3/1977 | Iler et al. |
| 4,138,336 A | | 2/1979 | Mendel et al. |
| 4,389,385 A | | 6/1983 | Ramsay |
| 4,600,646 A | | 7/1986 | Stout |
| 4,648,975 A | | 3/1987 | Barkatt et al. |
| 6,783,672 B2 | * | 8/2004 | Tubbs et al. ............. 210/198.2 |
| 2002/0094566 A1 | * | 7/2002 | Tubbs et al. ............. 435/287.2 |
| 2002/0160196 A1 | * | 10/2002 | Carr et al. .................. 428/407 |
| 2004/0007530 A1 | * | 1/2004 | McNeff et al. ............. 210/656 |

OTHER PUBLICATIONS

Barth, H. et al., "Column Liquid Chromatography," *Analytical Chemistry*, vol. 60, pp. 387R–435R (1988).

Clearfield, A. et al., "New Inorganic Ion Exchangers," *Ion Exchange and Solvent Extraction*, Marinsky et al. eds., Marcel Dekker, New York, vol. 5, pp. 1–119 (1973).

(List continued on next page.)

*Primary Examiner*—Ernest G. Therkorn
(74) *Attorney, Agent, or Firm*—Merchant & Gould P.C.

(57) ABSTRACT

The present invention describes the use of porous metal oxides for the preparative purification of antibodies and biomolecules within a range of particle physical characteristics. Typically, particles from 15 to 100 microns in average diameter with pores sizes ranging from 400 to 600 angstroms and surface areas from 10 to 50 square meters per gram, and pore volumes from 0.1 to 0.4 mL/gram can be used for purification processes. The metal oxide particles that fall within this range of physical properties show enhanced utility and greater chromatographic capacity for antibodies than materials oxide particles falling outside of this range. Metal oxides such as zirconia, titania and alumina can all be modified with a multi-Lewis base moiety such as an organophosphate ethylenediamine-N,N-tetra (methylenephosphonic) acid (EDTPA), to produce a biocompatible purification media for, biomolecules.

9 Claims, 13 Drawing Sheets

OTHER PUBLICATIONS

Sofer, G., "Preparative chromatographic separations in pharmaceutical, diagnostic, and biotechnology industries: current and future trends," *Journal of Chromatography A,* vol. 707, pp. 23–28 (1995).

Kopaciewicz, W. et al., Retention Model for High–Performance Ion–Exchange Chromatography, *Journal of Chromatography,* vol. 266, pp. 3–21 (1983).

Yang, Y. et al., "Coated hydrophilic polystyrene–based packing materials," *Journal of Chromatography,* vol. 544, pp. 233–247 (1991).

Yang, Y. et al., "Characterization of a novel stationary phase derived from a hydrophilic polystyrene–based resin for protein cation–exchange high–performance liquid chromatography," *Journal of Chromatography A,* vol. 723, pp. 1–10 (1996).

Lee, D., "Reversed–Phase HPLC from pH 1 to 13," *Journal of Chromatographic Science,* vol. 20, pp. 203–208 (1982).

Dawkins, J. et al., "Chromatographic Characteristics of Polymer–Based High–Performance Liquid Chromatography Packings," *Journal of Chromatography,* vol. 352, pp. 157–167 (1986).

Bowers, L. et al., "Solvent Strength Studies on Polystyrene-Divinylbenzene Columns," *Journal of Chromatography,* vol. 371, pp. 243–251 (1986).

Varady, L. et al., "Fimbriated stationary phases for proteins," *Journal of Chromatography,* vol. 631, pp. 107–114 (1993).

Unger, K. et al., "Oxide Stationary Phases," *High Performance Liquid Chromatography,* Brown et al. eds., Wiley, New York, Ch. 3, pp. 145–188 (1989).

Kawahara, M. et al., "Evaluation of New Ceramics as Column Packing Material for High Performance Liquid Chromatography," *Analytical Sciences,* vol. 4, pp. 671–673 (1988).

Kawahara, M. et al., "Titania and Zirconia as New Ceramic Column Packing Materials for High Performance Liquid Chromatography," *Analytical Sciences,* vol. 5, pp. 485–486 (1989).

Kawahara, M. et al., Titania and zirconia: possible new ceramic microparticulates for high–performance liquid chromatography, *Journal of Chromatography,* vol. 515, pp. 149–158 (1990).

Trudinger, U. et al., "Porous zirconia and titania as packing materials for high–performance liquid chromatography," *Journal of Chromatography,* vol. 535, pp. 111–125 (1990).

Nawrocki, J. et al., "Chemistry of zirconia and its use in chromatography," *Journal of Chromatography A,* vol. 657, pp. 229–282 (1993).

Amphlett, C. et al., "Synthetic Inorganic Ion–Exchange Materials–II Hydrous Zirconium Oxide and Other Oxides," *J. Inorg. Nucl. Chem.,* vol. 6, pp. 236–245 (1958).

Amphlett, C. et al., "Synthetic Inorganic Ion–Exchange Materials–I Zirconium Phosphate," *J. Inorg. Nucl. Chem.,* vol. 6, pp. 220–235 (1958).

Malm, B., "A method suitable for the isolations of monoclonal antibodies from large volumes of serum–containing hybridoma cell culture supernatants," *Journal of Immunological Methods,* vol. 104, pp. 103–109 (1987).

Jiang, Z. et al., "Synthesis of Porous Titania Microspheres for HPLC Packings by Polymerization–Induced Colloid Aggregation (PICA)," *Analytical Chemistry,* vol. 73, pp. 686–688 (2001).

Jones C., et al., "Current trends in molecular recognition and bioseparation," *Journal of Chromatography A.,* vol. 707, pp. 3–22 (1995).

* cited by examiner

FIG.1
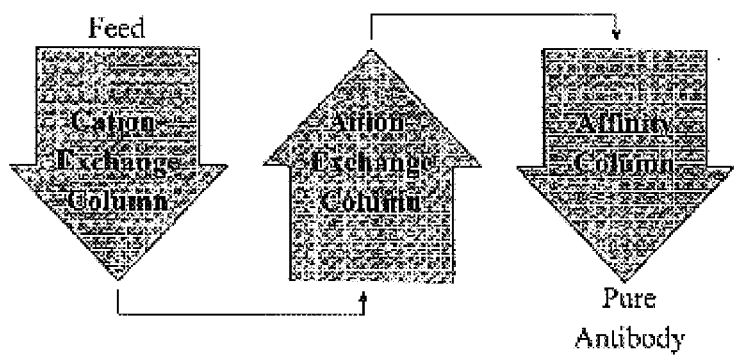
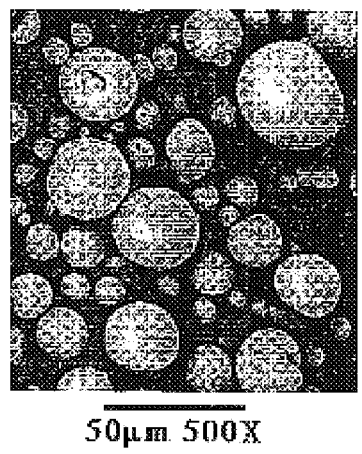
FIG.2
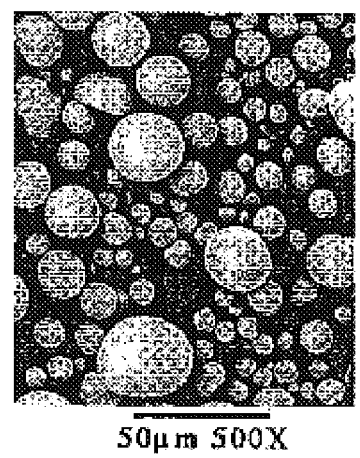
FIG.3

HIGH STABILITY POROUS METAL OXIDE SPHERULES USED FOR ONE-STEP ANTIBODY PURIFICATIONS

This application claims priority from provisional application Ser. No. 60/377,451, filed May 3, 2002, and which is incorporated herein by reference.

FIELD OF THE INVENTION

The present invention relates to metal oxide materials used in antibody and other purifications. More particularly, the present invention relates to modifying a metal oxide with a multi-Lewis base moiety such as ethylene-N,N-tetra (methylenephosphoric acid) ("EDTPA").

BACKGROUND OF THE INVENTION

There are increased market pressures on the healthcare industry to provide protein based therapeutics in ample amounts while being "specific pathogen free" ("SPF") and at reduced cost. Clinical validation is still an overriding cost to process restructuring as well as the introduction of new protein based drugs. Needs for increases in process efficiency include that of pre-purification steps and affinity adsorption processes which can select for desirable protein populations. Affinity and ion exchange adsorption technology are scaleable technologies important to protein purification. Ideally, a new adsorption technology will have high selectivity, yield, throughput, and will be amenable to or directly provide improved specific pathogen removal, minimized buffer usage, minimized operating complexity, and also be less expensive to produce than current matrices. Therefore, specific advantages imparted by new matrix technologies should be amenable to process validation.

I. Inorganic Oxide-Based Chromatographic Supports

Currently known inorganic chromatography supports comprising particulate silica ($SiO_2$) or alumina ($Al_2O_3$) are stable over pH ranges of about 1–8 and 3–12, respectively. The solubilization of $SiO_2$ and $Al_2O_3$ at pHs outside of these ranges results in deterioration of these supports and contamination of the resultant chromatographed and separated products with silicon- or aluminum-containing species. Methods of improving the alkaline stability of particulate $SiO_2$ by cladding the surface with a more base stable metal oxide such as zirconium oxide ($ZrO_2$) have been disclosed in U.S. Pat. Nos. 4,648,975 and 4,600,646. This cladding is disclosed to increase the upper pH limit at which these supports, also referred to as packings, can be used to 11 and 9.5, respectively. However, these packings still lack adequate stability to allow them to be sterilized and cleaned in, for example, 0.1N aqueous sodium hydroxide (NaOH, pH=13).

Use of porous spherical $ZrO_2$ particles on a thin layer chromatography plate has been disclosed in U.S. Pat. No. 4,138,336, a process for the preparation of porous $ZrO_2$ microspheres is taught in U.S. Pat. No. 4,010,242, and chromatographic use of these particles is taught in U.S. Pat. No. 3,782,075. The microspheres are prepared by a process in which colloidal metal oxide particles are mixed with a polymerizable organic material and coacervated into spherical particles by initiating polymerization of the organic material. This is a time consuming, batch process which requires the addition of organic material which is pyrolized and hence lost.

U.S. Pat. No. 3,862,908 discloses microspheres of urania and other metal oxides; however, these particles are fired to near full density, have reduced surface areas and therefore, would not be attractive for chromatographic uses.

U.S. Pat. No. 3,892,580 discloses a process for preparing porous bodies of $ZrO_2$. This process requires the use of a binder to react with the oxide particles during preparation. This binder is subsequently decomposed by pyrolysis and therefore lost. The bodies produced by this process are not spherical, would pack unevenly, may cause increased column pressure, and are therefore not attractive for chromatographic uses.

U.S. Pat. No. 4,389,385 teaches the preparation of porous gels and ceramic materials by dispersing solid particles of an inorganic substance produced by a vapor phase condensation method in a liquid to form a sol. The sol contains colloidal particles which are aggregates of the primary particles. The sol is dried to produce a porous gel of greater than 70% by volume porosity.

The eluent, also referred to as the mobile phase, used to elute the various components from the stationary phase is relatively polar, e.g., an aqueous buffer or a mixture of water and an organic solvent, e.g., aqueous alcohol. Its polarity can be changed by increasing the concentration of the less polar liquid in the mobile phase, a technique known in the art.

Thus relative to the use of $ZrO_2$-clad silica, a more promising approach to developing a highly stable reversed-phase support, involves replacing the silica with an alternative inorganic material, such as alumina. Although it has been demonstrated that some improvement in pH stability is realized by replacing silica with alumina, the dissolution of alumina in aqueous solutions at extreme pHs (pH<2 and pH>12), even at room temperature, is well known.

As mentioned previously, in addition to the use of a pH-stable support material, the production of a stable, reversed-phase also requires a process for modifying the support material which results in a stable, hydrophobic surface. Silylation is the most widely used method to derivatize silica particles to produce hydrophobic reversed-phase supports. The silylation of inorganic bodies other than silica (e.g., alumina, titania, zirconia, etc.) has been disclosed in U.S. Pat. No. 3,956,179. However, it is uncertain whether or not covalent bonds to the support surface are actually formed. In any event, the hydrolytic instability of the siloxane bond is well known, and it is very likely that a Si—O-metal bond will be even more susceptible to aqueous hydrolysis because of the increased polarity of the bond.

An alternate approach to silylation for modifying the surface polarity of inorganic bodies is the sorption of a polymer of desired polarity/functionality onto an $SiO_2$ or $Al_2O_3$ support surface followed by cross-linking of the individual polymer chains to one another to impart additional stability to the coating. Reversed-phase supports prepared in this fashion exhibit much improved pH stability compared to those prepared by silylation. It is important to recognize that the formation of a stable, cross-linked polymer layer on the surface of the support does not reduce the need for a stable, inorganic support, since it may not be possible to cover the entire inorganic surface. Although cross-linking of the polymer may keep it in place even as the underlying inorganic support dissolves, dissolution of the support will undoubtedly lead to a reduction in the mechanical stability of the support. In addition, problems related to increasing column back pressure are known to accompany the dissolution of the inorganic support and its subsequent appearance in the mobile phase and transport through the column and the accompanying instrumentation.

Another problem related to the use of silica-based reversed phase supports is the difficulty encountered in the chromatography of amines and other basic solutes. This problem results from the presence of acidic silanol groups (SiOH) on the silica surface. Basic solutes undergo very strong interactions with these silanol groups which may involve cation exchange or hydrogen bonding, depending on the pH of the mobile phase. This problem is exaggerated by the requirement of working in the pH range 2<pH<8 on silica-based columns, since most amines will be protonated in this pH range and protonated amines can readily bond to the silica surface. One obvious approach to improving the chromatography of amines is to work at hydrogen ion concentrations significantly lower than the ionization constant of the amines so that they are unprotonated. For aliphatic amines, this normally involves working at a pH greater than 11. However, these pH ranges cannot be employed using silica-based columns.

The presence of the aforementioned acidic silanol groups can also lead to irreversible adsorption of many classes of organic molecules onto silica-based reversed-phase supports, a problem which is well known to those versed in the art. This irreversible adsorption is can be particularly troublesome in the reversed-phase HPLC of proteins. Ultimately, this adsorption will result in a change in the properties of the support and can lead to its destruction. Thus, alternative materials are desired for chromatographic separations.

II. Ion-Exchange High Pressure Liquid Chromatography

Ion-exchange chromatography (IEC) has become an important separation technique for the purification of biomolecules. Typical supports used in IEC are silica, alumina, agarose, polymethacrylate, and poly (styrenedivinylbenzene). See H. G. Barth et al., *Anal. Chem.*, 60, 387R (1988). Agarose is not suitable for high pressure work, while silica and alumina have limited pH stability. The matrices of silica and alumina must also be derivatized or coated to provide the support with ion exchange properties. This often introduces hydrophobic interactions into the retention mechanism. The hydrophobic nature of hydrocarbon-based supports such as poly(styrene-divinylbenzene) must be masked in order for them to be used as IEC supports. The hydrocarbon-based supports are also subject to shrinking and swelling whereas inorganic supports are not.

Zirconium phosphate has been extensively studied as an inorganic ion exchanger for the nuclear industry because of its excellent exchange capacities, radiation and thermal stability. See A. Clearfield et al., *Ion Exchange and Solvent Extraction*, J. A. Marinsky et al., eds., Marcel Decker, New York, (1973) at Chapter 1.

Ion-exchange chromatography is the leading technique in the purification of proteins [Sofer, G., *J. Chromatogr.*, 707 (1995), 23.]. Mobile phase conditions used in the ion-exchange mode are generally non-denaturing leading to high recoveries and retention of biological activity encountered when purifying bio-polymers by this method [Kopaciewicz, W., Rounds, M. A., Fausnaugh, J. and Regnier, F. E., *J. Chromatogr.*, 266 (1983), 3.]. In addition, elution profiles are relatively predictable facilitating scale up [Yang, Y.-B. and Regnier, F. E., *J. Chromatogr.*, 544 (1991), 233.].

The popularity of ion-exchange chromatography for protein purification has grown with advances in ion-exchange stationary phase supports [Yang, Y.-B., Harrison, K. and Kindsvater, J., *J. Chromatogr.*, 723 (1996), 1.]. This progression towards better ion-exchange materials, and column packings in general, includes changes in the base support material. Agarose and silica based phases are being used less in favor of highly crosslinked polystyrene divinylbenzene (PS-DVB) [Sofer, G., *J. Chromatogr.*, 707 (1995), 23., 8–11; Lee, D. P., J. Chromatogr. Sci., 20 (1982), 203.; Dawkins, J. V., Lloyd, L. L. and Warner, F. P., *J. Chromatogr.*, 352 (1986), 157.; Bowers, L. D. and Pedigo, S., *J. Chromatogr.*, 371 (1986), 243.; L. Varaday, N. Mu, Y.-B. Yang, S. E. Cook, N. Afeyan and F. E. Regnier, *J. Chromatogr.*, 631 (1993) 107.] as well as metal oxide supports such as alumina, titania [K. K. Unger, in P. R. Brown and R. A. Hartwick (Editors), *High Performance Liquid Chromatography*, Wiley, New York, 1989, Ch. 3, p. 145.] and zirconia [M. Kawahara, H. Nakamura and T. Nakajima, *Anal. Sci.*, 4 (1988), 671.; M. Kawahara, H. Nakamura and T. Nakajima, *Anal. Sci.*, 5 (1989), 485.; M. Kawahara, H. Nakamura and T. Nakajima, *J. Chromatogr.*, 515 (1990), 149.; U. Trüdinger, G. Müller and K. K. Unger, *J. Chromatogr.*, 535 (1990), 111.; J. Nawrocki, M. P. Rigney, A. V. McCormick and P. W. Carr, *J. Chromatogr.*, 657 (1993), 229.] owing to the increased pH and thermal resistance of newer supports towards dissolution, and their ability to accommodate organic solvents without shrinking or swelling [C. B. Amphlett, L. A. McDonald and M. J. Redman, J., *Inorg. Nucl. Chem.*, 6 (1958), 236.; C. B. Amphlett, L. A. McDonald and M. J. Redman, J., *Inorg. Nucl. Chem.*, 6 (1958), 220.; N. Michael, W. D. Fletcher, D. E. Croucher and M. J. Bell, *Report CVNA-135, Carolina-Virginia Nucl. Power Assoc.*, Charlotte, N.C., 1961.].

A widely used method for the preparative purification of antibodies [Malm, B., "A Method Suitable for the Isolation of Monoclonal Antibodies from Large Volumes of Serum-Containing Hybridoma Cell Culture Supernatants," *J. Immunological Methods*, 104 (1987), 103–109.] involves the use of three LC columns, first a cation-exchange column, followed by an anion-exchange column and finally an affinity column as the final purification media. This method is depicted in FIG. 1. This purification protocol is extremely time-consuming, but the final product is adequately pure (>95%). The first two columns in the purification protocol are an anion-exchange and a cation-exchange column. These two columns are used as initial clean-up columns and are followed by an affinity column that specifically binds and then releases the pure monoclonal antibody.

A single EDTPA modified metal oxide column offers a cost-effective alternative to this three column approach. Furthermore, the extreme stability of zirconia stationary phases makes the media sterilizable and cleanable thereby further reducing antibody production costs. The main benefits, among others, of metal oxide-based Mab purification media are:

1. New Cost-Effective Alternative to Protein A and Protein G Affinity Chromatographic Media;
2. Particles are Made from Inert Zirconium Dioxide with A Non-Animal Source Stationary Phase;
3. Particles are Chemically Stable in Acid and Base Solutions, which Allows for Depyrogenation and Cleaning of Particles;
4. Rigid Particles Allow for Use of High Linear Velocities for Unparalleled Product Throughput;
5. Useful for a Variety of Immunoglobulins Including IgGs, IgA and IgMs;
6. Does Not Bind Serum Proteins that can "Foul" Protein A and Protein G Media;
7. Tunable Selectivity for Different Immunoglobulins Using pH and Ionic Strength as the Main Variables;
8. Antibody Purity Levels As Good or Better than Protein A and Protein G Media;
9. Extended Media Lifetime Compared to Protein A and Protein G Media;
10. High Binding Capacity for Immunoglobulins to Protein A and Protein G Media.

SUMMARY OF THE INVENTION

The present invention provides a support material adapted for use as the stationary phase in large scale (preparative) liquid chromatography. The materials comprises porous spherules of metal oxides (zirconia, titania and alumina). All these particles (both spherical or irregular shaped) display extended chemical stability in aqueous media of a pH compared to silica gel-based stationary phases.

These particulate spherules can be formed into a bed, and employed as the stationary phase in separations performed via chromatography. Therefore, the spherules can be used as the stationary phase in conventional chromatography columns that have an axial flow path, with or without rigid walls. For example, the porous metal oxide particles can be packed into a column such as a HPLC column, where the packing functions as the stationary phase during HPLC separations that are accomplished by ion exchange. The spherules can also be used in columns that have a radial flow path or to form a fluidized bed, with single or multiple stage absorbers.

The particulate spherules can be modified with ethylene-N,N-tetra (methylenephosphoric acid) ("EDTPA") or other multi-Lewis base moieties to provide a system for purification or separation of biomolecules such as immunoproteins. This system requires only one chromatographic column and provides an effective separating method.

The coated spherules can also be combined with a suitable binder and used to coat a glass or plastic substrate to form plates for thin-layer chromatography.

In addition, "irreversibly adsorbed" organic or biological residues can be removed from fouled columns packed with coated or uncoated spherules by flushing the column with a mobile phase at high pH or by injecting pulses of the high pH mobile phase. The term "irreversible adsorption" refers to the very strong tendency which surface-adsorbed proteins, biopolymers and the like exhibit to remain sorbed under normal elution conditions, until the mobile phase conditions are changed sufficiently to desorb them.

The metal oxide particles may also be exposed in situ to traditional sterilization conditions, for example, by exposing the packing or the packed column to heat and high pH, without significant degradation.

The above summary of the present invention is not intended to describe each disclosed embodiment or every implementation of the present invention. The Figures and the detailed description that follow more particularly exemplify embodiments of the invention. While certain embodiment of the invention will be illustrated in describing embodiments of the invention, the invention is not limited to use in such embodiments.

BRIEF DESCRIPTION OF THE DRAWINGS

FIG. 1 is a schematic of a multiple column liquid chromatography method of antibody purification;

FIG. 2 is an exemplary SEM of preparative zirconia particles, containing 1% zirconyl sulfate binder, spray dried at Aero-Instant;

FIG. 3 is an exemplary SEM of preparative zirconia particles without binder, spray dried at Aero-Instant;

Figure 4:
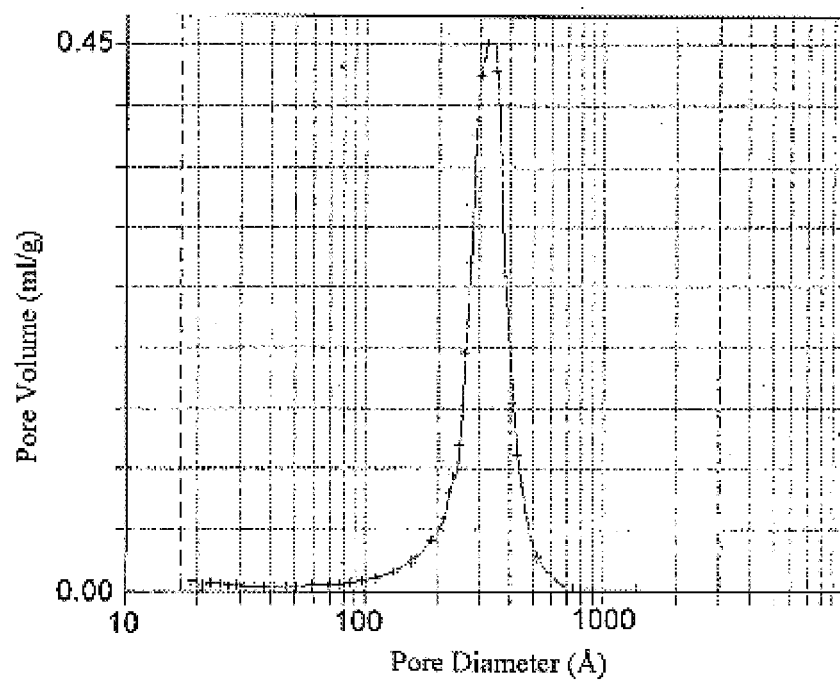
FIG. 4 is an exemplary plot of dV/dlog (D) adsorption pore volume plot of spray dried zirconia particles without binder.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE PREFERRED EMBODIMENTS

Generally, the present invention relates to modifying a metal oxide such as zirconia, titania, and alumina with ethylene-N,N-tetra (methylenephosphoric acid) for the separation of immunoproteins.

Other metal oxide materials include hafnia, ceria, yttria or magnesia. Other modifying agents are any suitable multi-Lewis base moiety, including, but not limited to, a metal chelator, a polycarboxylate, a polyphosphate such an inorganic phosphate. The modifying agent, such as a phosphate, can be incorporated into the surface of the metal oxide and may comprise between about 0.5–15% by weight, preferably 2–12% by weight.

I. Preparation of Modified Metal Oxide Microspheres

Generally, zirconia microspheres were generated by spray drying colloidal zirconia. Spray-dried zirconia microspheres were further classified and characterized by X-ray diffraction, BET porosimetry and scanning electron microscopy. The zirconia microspheres were also modified with ethylenediamine-N,N-tetra (methylenephosphonic acid) ("EDTPA") to create a cation-exchange chromatographic support. The chromatographic behavior of semi-preparative columns packed with EDTPA-modified zirconia microspheres was studied. EDTPA-modified zirconia microspheres were further used to purify Mabs from cell culture supernatants. Analysis by enzyme linked immunosorbent assay and gel electrophoresis demonstrate that Mabs can be recovered from a cell culture supernatant at high yield (92–98%) and high purity (0.95%) in a single chromatographic technique. The retention of pure Mab samples was also shown on EDTPA modified porous zirconia, titania and alumina materials. Finally, greater chromatographic capacity was shown for zirconia and titania materials that fall within the physical characteristics described herein.

Preferred metal oxide spherules are particles from about 3–100 microns in average diameter with pores sizes ranging from about 200 to 1200 angstroms and surface areas from about 3–30 square meters per gram, and pore volumes from about 0.1 to 0.4 mL/gram, most preferably about 15–30 m.sup.2/g; and have pore diameters of from about 450–1000 ANG., most preferably about 500–1000 ANG.

In another embodiment, the present invention provides a stable stationary phase for chromatography that includes porous metal oxides (including zirconia, titania and alumina) spherules coated with EDTPA wherein said coated spherules have a typical pore size from about 200–600 ANG. and a particle diameter range of about 20–100 microns and have superior pH stability to silica gel stationary phases.

A. Production of Preparative Porous Zirconia by Spray Drying

Spray drying is a single-step continuous particle-processing operation that transforms a feed in the form of a solution or suspension of solid particles into particulate form. The spray dried end product may be in a powdered, granular or in an agglomerated form. The conformational state of the end product depends on the physical and chemical properties of the feed, dryer design and mode of operation. Spray drying involves atomization of the feed into a current of hot gases resulting in moisture evaporation. By atomizing the feed a large interfacial area is produced and consequently a high rate of evaporation is obtained. The performance of a spray dryer depends critically on the droplet size produced by the atomizer and the efficiency of heat transfer between the droplets and the gaseous medium. The advantages of spray drying include its ability to produce powders or granules of specific particle size and moisture content, applicability to both heat-sensitive and heat-resistant materials and its ability to handle feedstocks in solutions, slurry, paste or melt form.

Preparative porous zirconia can be produced through spray drying using the following method. A 20% (w/v) colloid (Nyacol, Ashland, Mass., USA) is the preferred starting materials, but the zirconia colloid concentration can be from 5–30%. Two types of particles were synthesized using (1) colloid that contained 1% (w/v) zirconyl sulfate and (2) colloid with no additives. The thought here was to see if the addition of a binder would augment the final particles chemical and mechanical strength. Due to previous unrelated research on making larger zirconia particles by an oil-emulsion process we knew that particle stability might be an issue for larger porous particles. Preliminary spray drying runs were conducted to optimize the nozzle size and the inlet temperature. A three-foot, extended height, gas-fired Bowen spray dryer outfitted with a twin-fluid nozzle was used in the preliminary experiments. The size of the nozzle seemed to have very little effect on the resulting particle size. Peristaltic silicone tubing was used to deliver the feed to the nozzle and care was taken to avoid any brass fittings or fixtures. Based on these preliminary experiments the following conditions were chosen for spray drying a 20% sol of zirconia:

| | |
|---|---|
| Inlet temperature | 135° C. |
| Outlet temperature | 75° C. |
| Air flow | 4.5 inches of water |
| Pump speed | 140 ml/min |

For the ease of scale up, a rotary atomizer was used to spray dry five gallons each of pure zirconia sol and zirconia sol with binder. A four-foot Niro utility spray dryer equipped with a NIO FU11 low vaned wheel rotary atomizer and a single-point product collection was used. The particle size distribution was determined using a MicroTrac particle size analyzer. The particle size of the as-made preparative zirconia with and without binder was 17.5±12.2 microns and 21.8±11.7 microns, respectively. The presence of the binder resulted in a lower average particle size, but the particle sizes are so polydisperse that there is no statistical difference. As shown later, there was a large difference between the average pore size of the particles spray dried with and without binder.

The total yield of zirconia particles (with and without binder) that was spray dried from 5 gallons of zirconia colloid (70% large) was 3940 g (67%) and 4020 g (74%), respectively. As shown in FIGS. 2 and 3, the spray dried zirconia particles (with and without the zirconyl sulfate binder) are polydisperse and relatively spherical with relatively few doughnuts present. There is a wide size distribution for both the zirconia particles with and without binder, but screening can narrow the size range with standard mesh sieves.

Both batches of zirconia particles (with and without binder) were then burned and sintered using an identical heating protocol. The zirconia particles were first heated in ten 20 gram batches, in ceramic crucibles, at 400° C. for 4 hours in a furnace (ThermoLyne 30400) using a linear temperature ramp-up of 5° C./min. Then, the burned zirconia particles were hardened and sintered at 750° C. for 6 hours and at 900° C. for 3 hours in the same furnace, using a linear temperature ramp-up of 20° C./min between each temperature. The particles were allowed to cool to room temperature and were then screened using a CSC Scientific sieve shaker. Two U.S.A. standard sieves, one 25 micron mesh and one 38 micron mesh, were used to a size-fractionate the zirconia particles. The final yield of burned and sintered zirconia particles in the size range of 25–38 microns in diameter for the zirconia particles made with and without binder was 1380 g (35%) and 1490 g (37%), respectively.

Physical Characterization of the Spray Dried Zirconia

1. BET Nitrogen Porosimetry

The surface area, pore size distribution, and pore volume of the preparative zirconia particles with and without binder are shown in Table 1. The measurements were performed on a Mircomeritics ASAP 2000 sorptometer. Prior to analysis, the zirconia samples were heated at 120° C. under vacuum for 6 hours to remove any adsorbed gases and moisture. The preparative zirconia particles made with binder had twice as much surface area than those made without binder. However, the zirconia particles made with binder had a low average pore size of 130 Å, which was much smaller than the 260 Å average pore size of the particles made without binder.

TABLE 1

Data from nitrogen porosimetry experiments

| Zirconia particles (25–28 microns) | Surface Area[a] ($m^2$/g) | Pore Volume[b] (ml/g) | Average Pore Diameter[c] (Å) |
|---|---|---|---|
| With binder | 33.2 | 0.106 | 130 |
| Without binder | 16.1 | 0.103 | 260 |

[a]From nitrogen adsorption using BET model,
[b]From single point estimation,
[c]From 4V/A estimation 2. X-ray Diffractometry All measured peaks in the diffraction pattern on the preparative zirconia sample correspond closely both in position and relative intensity to the peaks predicted for a well formed monoclinic crystal of zirconia; thus, we conclude that the sample is pure, well formed monoclinic zirconia as is the PICA based material. (The absence of extraneous means that the material is pure and monoclinic).

If the relative peak intensities were not in good agreement with those predicted (but the positions were still correct) the crystals might not be well formed, that is, possess sufficient length, width and height to yield statistically determined reflections for all planes. This is not the case here. Moreover, if some peaks that were much broader than others, this would suggest poor crystal formation (e.g. very thin needles or slabs). Again this is not the case.

B. EDTPA Modification Procedure

Porous metal oxides can be surface modified with a phosphate, such as organic and inorganic phosphates, that can be derived from, for example, a phosphoric acid or an alkali metal phosphate salt. An example of a phosphate used in the modification of the ethylenediamine-N,N'-tetra (methylphosphonic acid) (EDTPA) by the following general method.

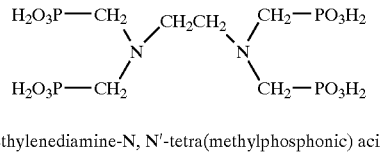

ethylenediamine-N, N'-tetra(methylphosphonic) acid

The specific case of zirconia as the metal oxide support will be used for demonstration purposes, but this method may also be applied to titania and alumina (of the same surface area and porosity).

Zirconia, titania and alumina all have a great affinity for inorganic and organic phosphates due to their strong Lewis acidities. Thus the coating of strong Lewis bases such as EDTPA are easily achieved by, for example, the following procedure: 20 g of zirconia particles are placed in 500 mL round-bottomed flasks and suspended in 200 mL of 0.1 M $H_4$EDTPA. The particles are sonicated under vacuum to allow the solution to fully infiltrate the pores, and then refluxed. Mixing is achieved by allowing the solution to boil. After four hours the reaction vessel is removed from the heat source and the particles are allowed to settle, and then the EDTPA solution is decanted. The particles are suspended in water and filtered and washed several times with water. The resulting cake of particles is dried at 50° C. in a clean vacuum oven overnight.

In another method, the EDTPA modification was performed by placing 50 grams of preparative zirconia in a 500 ml round-bottomed flask and suspending the particles in 250 ml of a 0.2 M solution of EDTPA (pH=2.5). The suspended particles were sonicated under vacuum for 1 minute. The vacuum was then broken and the sonication process was repeated twice to ensure that the EDTPA solution fully infiltrated the pores. The solution was then refluxed for 4 hours; mixing was achieved by allowing the solution to bump. After the refluxing period, the particle mixture was removed from the heating source and allowed to cool and settle. Once the solution was at room temperature, the EDTPA solution was decanted. The particles were re-suspended in 200 ml of HPLC grade water. The water was decanted after the zirconia particles settled and the whole process was repeated twice. The particles were then suspended in 200 ml ethanol and were transferred to a sintered glass funnel. The particles were washed with an additional 200 ml ethanol and air was pulled through the bed until the particles were free flowing.

Figure 5:
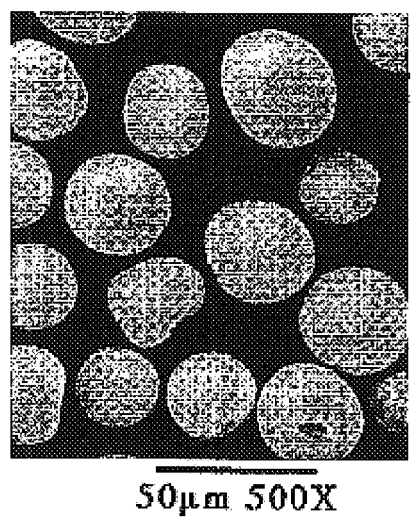
FIG. 5 is an exemplary SEM of screened EDTPA-modified spray dried zirconia.

Finally, the dried EDTPA-modified zirconia particles were re-screened with the 25 and 38 micron mesh sieves. The final yield of modified and screened zirconia particles was 30 g, which means the total process from beginning to final modified particle is 22.2% efficient. Elemental analysis was performed to determine percent carbon and phosphorus which was 0.29% and 0.24%, respectively. This corresponds to a surface coverage of 1.2 μm per square meter of EDTPA, which compares nicely to the 0.6–3.0 range of coverage reported on analytical scale EDTPA modified PICA zirconia. A scanning electron micrograph of the EDTPA-modified, re-screened zirconia particles, that is the final particles, is shown in FIG. 5.

Analytical scale (15 cm×4.6 mm i.d.) HPLC columns were packed with the preparative EDTPA-modified zirconia particles using a downward slurry method at a pressure of 1200 psi. Isopropanol was used as both the slurry and chaser solvent. The 15×1 cm i.d. semi-preparative columns were packed using a dry packing method.

Figure 6:
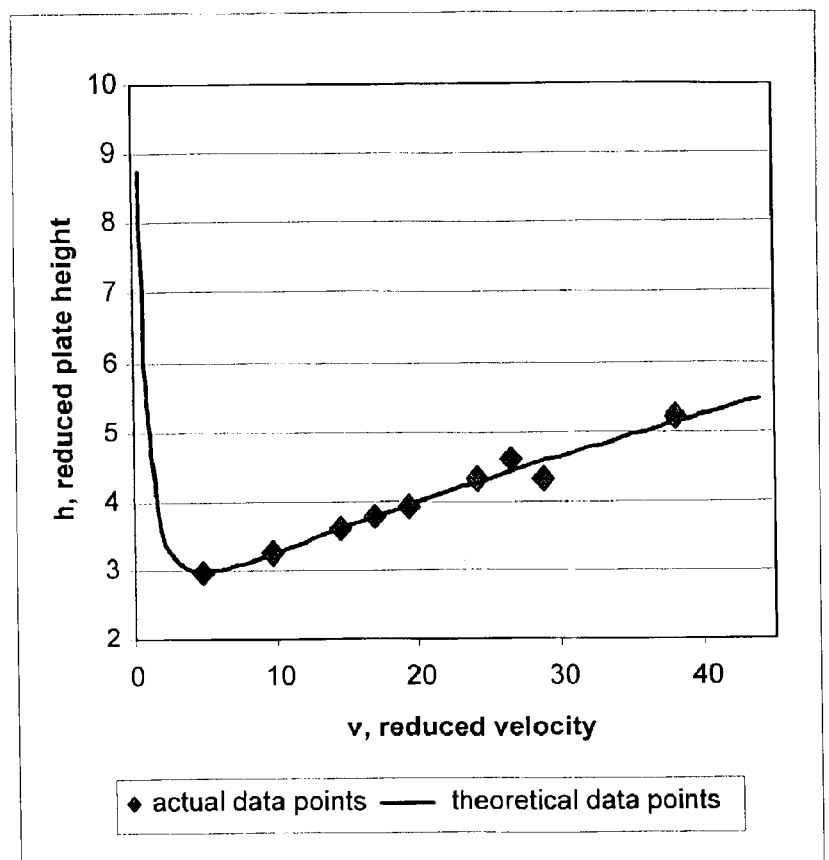
FIG. 6 is an exemplary plot of a flow study for a 15×1 cm EDPTA-modified spray dried zirconia fit to the Knox equation.

II. Chromatographic Characterization of Preparative EDTPA-Modified Zirconia Particles In order to test the chromatographic behavior of the EDTPA modified zirconia columns a flow study was done in order to measure the dependence of column efficiency on mobile phase flow rate. This data was then analyzed in light of the Knox equation, $h = Av^{1/3} + B/v + Cv$. This is an empirical equation used to quantify three band broadening processes, namely eddy dispersion ($Av^{1/3}$), longitudinal diffusion (B/v), and resistance to mass transfer (Cv) in liquid chromatography. In this experiment, the Knox coefficients A, B and C, were determined for a 15×1 cm semi-preparative column, packed with EDTPA-modified spray-dried zirconia without binder. The mobile phase was a solution of 4 mM EDTPA, 20 mM MES and 5 mM NaCl. Nine flow rates were used: 0.5, 1.0, 1.5, 1.75, 2.0, 2.5, 2.75, 3.0, and 4.0 ml/min. The probe solute used for this flow study was 4-dimethylaminopyridine, which had an average retention factor of 0.97. FIG. 6 shows a plot of the reduced plate height versus reduced flow velocity. The Knox coefficients were evaluated using multivariate linear regression. An A-term of 1.2 was obtained from the regression analysis. The A-term is related to the peak broadening due to eddy dispersion and is thus related to how well a column is packed. An A-term of close to 1.0 indicates a well packed column. The B coefficient, which describes band broadening due to longitudinal diffusion, had a value of 3.9. B-term values larger than about 2 is in theory impossible, and therefore experimental values larger than about 2 are likely due to some contribution from the packing term (A-term). Our value of 3.9 suggests that there is some channeling in the column. This is to be expected in small columns packed with large particles where there will likely be channeling at the column wall (where the randomly packed bed is abruptly interrupted). This "wall-effect" should be reduced in the larger diameter columns that will be tested in phase II research. However, since the column will be operated at high linear velocity the B-term is not very important in preparative chromatography. The C coefficient was 0.024. It results from band broadening from resistance to mass transfer of the solute in the stationary phase. The value obtained here is good and indicates that there is only a weak dependence of column efficiency on mobile phase velocity.

Figure 7:
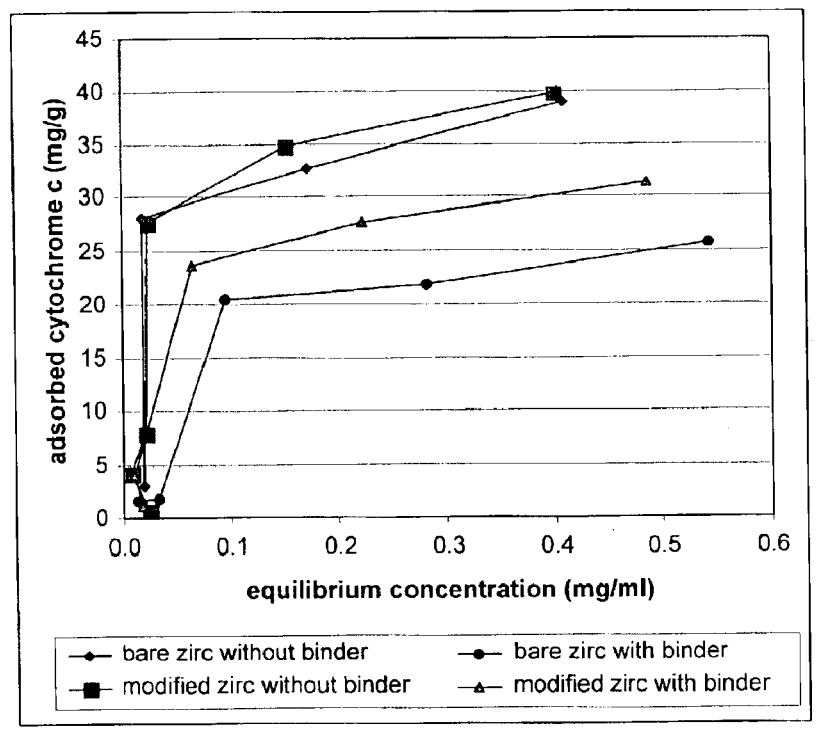
FIG. 7 is an exemplary plot of static adsorption isotherms for 4 types of spray-dried zirconia.

III. Static and Dynamic Binding Capacity of a Model Protein on Preparative Zirconia Particles Cytochrome c was chosen as a model protein (since it is cationic) to measure the binding capacity of preparative zirconia particles. This study also allowed us to compare our results to previous work on analytical-scale PICA particles [Clausen Paper]. Static binding capacity of cytochrome c of 4 types of zirconia, bare zirconia with and without zirconyl sulfate binder and EPDTA-modified zirconia with and without 1% zirconyl sulfate binder was determined by a similar method to that previously described. A stock solution of 50 mg of cytochrome c in 50 ml of 20 mM MES, 4 mM EDTPA buffer adjusted to a pH 5.5, was made. Standard solutions of 0.005, 0.01, 0.03, 0.05, 0.1, 0.2, 0.3, 0.5, and 0.8 mg/ml were serially diluted from the stock solution. A standard curve was made from these solutions. 50 mg of each type of zirconia was placed in 15 ml polypropylene centrifuge tubes. 5 ml of each dilute solution was added to each different type of zirconia. The tubes were shaken once every 15 minutes for 2 hours, after which they were centrifuged. The absorbance of the supernatant and standard solutions at 280 nm was performed on a HP 8452A Diode Array Spectrophotometer. Using the standard curve, the amount of cytochrome c absorbed by the zirconia was determined as shown in FIG. 7. The static binding capacity was determined by plotting the static adsorption isotherm for each zirconia type. None of the four types of zirconia were completely saturated with cytochrome c, as shown by the upward slope of each isotherm. However, an estimate of the static binding capacity was obtained by extrapolation. The binder-free EDTPA-modified spray-dried zirconia particle are comparable to the 3 μm analytical scale EDTPA-modified zirconia particles, which have an estimated static binding capacity of 40 mg cytochrome c per gram of zirconia.

The dynamic binding capacity was determined using an 50×4.6 mm HPLC column packed with 1.63 g of binder-free EDTPA-modified zirconia. The HPLC system used for this experiment consisted of an Altex 110A HPLC pump, a Perkin-Elmer LC 15 UV detector (254 nm), and a Hewlett Packard 3396A integrator. A 1.0 mg/ml solution of cytochrome c was made using a 20 mM MES, 4 mM EDTPA buffer at pH 5.5. The dead volume of the system with the column was determined using a 0.25% acetone (w/v) in buffer solution. The column was flushed with buffer until a flat baseline was achieved. The pump outlet was then detached from the rest of the system, and the acetone solution was flushed through the system up to the pump outlet. The pump outlet was then reattached to the column, and the time for the baseline to increase was measured. The dead volume was measured as 0.6 ml for our system. Using the same protocol, the dynamic binding capacity was determined using the 1.0 mg/ml cytochrome c solution. When the column was saturated by cytochrome c, the detector measured the protein breakthrough curve at 47.2 ml. The difference between this volume and the dead volume gives the dynamic binding capacity of the column. It was determined that the dynamic binding capacity of EDPTA-modified zirconia without binder was 28.6 mg of cytochrome c per gram of zirconia. As expected, this is lower, but not drastically so than the static capacity.

IV. Chemical Stability of Preparative EDTPA-Modified Zirconia

Figure 8:
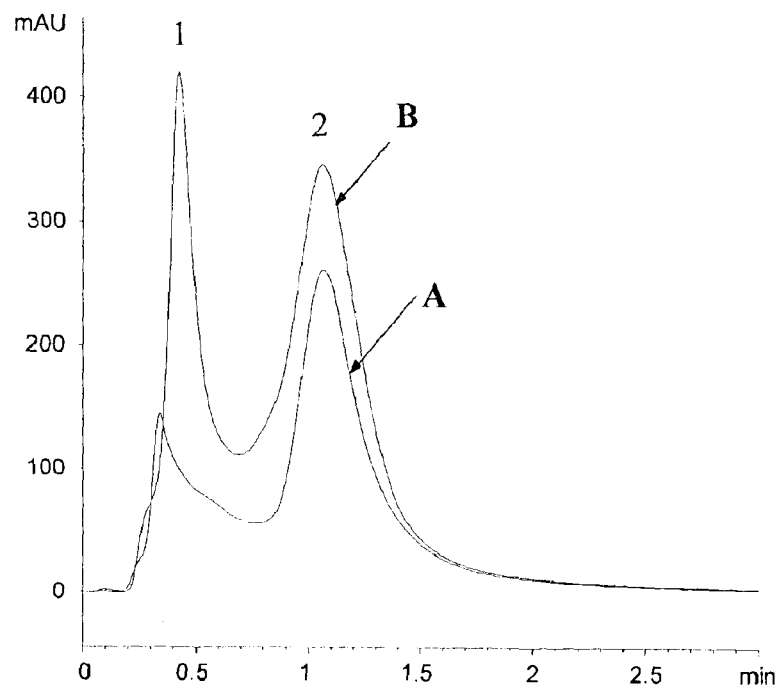
FIG. 8 is an exemplary plot of the separation of 2-hydroxypyridine (1) and 2,6-diaminapyridine (2) prior to flushing with acid and base (A) and after regenerating the column (B)

The chemical stability of the EDTPA-modified zirconia particles without binder was tested prior to the purification of monoclonal antibodies. Two pyridine derivatives were separated on an analytical scale column (150×4.6 mm) packed with the spray-dried modified zirconia particles. Following the injection of the pyridine derivatives, the column was flushed with 100 column volumes of 0.1M sodium hydroxide and 100 column volumes 0.1M nitric acid. After flushing with acid and base, the column was regenerated by pumping a buffer containing 20 mM MES, 4 mM EDTPA, and 5 mM NaCl pH at 5.5 through the column for 72 hours at 0.5 ml/min and 60° C. As shown in FIG. 8, which shows the separations of the pyridine derivatives before and after flushing the column with acid and base, there is no loss in retention of the probe solutes, and thus no loss on stationary phase. The conditions for the separation are: Mobile phase: 20 mM MES, 4 mM EDTPA, 5 mM NaCl pH=5.5; Flow rate: 2.0 ml/min; Temperature: 30° C.; and Detection: 254 nm. Furthermore, inspection of the column inlet showed that there was no void formation. We conclude that EDTPA-modified spray dried zirconia is stable over a pH range of 1 to 13.

Figure 9:
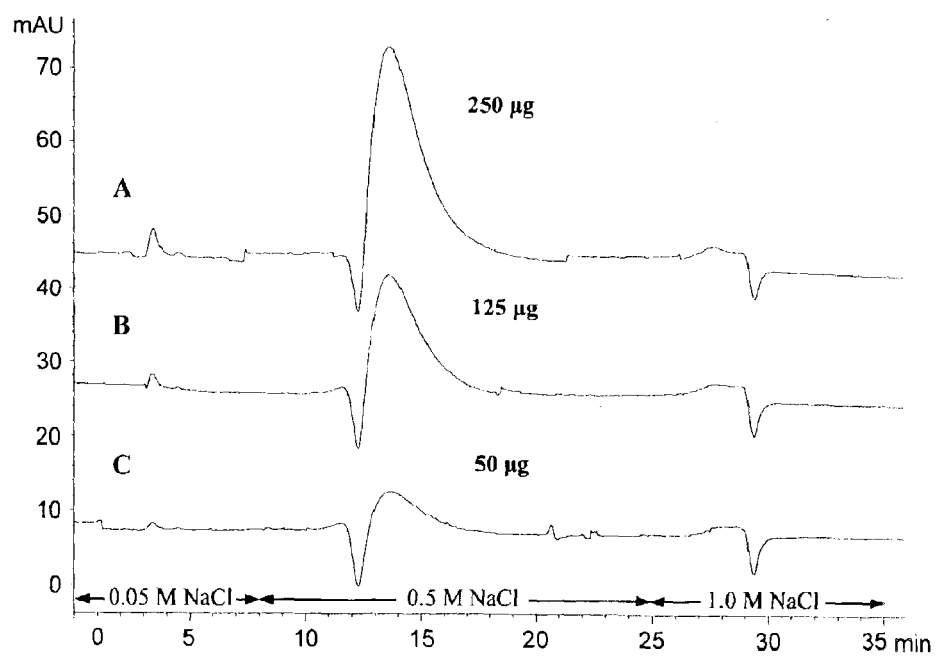
FIG. 9 is an exemplary plot of three different size injections of Mab eluted using salt step gradient elution.

V. Injection of Pure Monoclonal Antibody on a Semi-Preparative EDTPA-Modified Zirconia Column Pure monoclonal antibody was eluted on a 15×1 cm i.d. semi-preparative column packed with EDTPA-modified zirconia particles (without binder). The antibody was loaded onto the column in a loading buffer containing 20 mM MES, 4 mM EDTPA, 50 mM NaCl at pH 5.5. The Mab was then eluted in the same buffer, but at a higher salt concentration (0.5 M NaCl). After the Mab eluted, the column was cleaned with the same buffer containing an even higher salt concentration (1.0 M NaCl). FIG. 9 shows three injections of pure Mab to demonstrate the separation of pure Mab and the loading capacity. The conditions for the injections are: Mobile phase: 20 mM MES, 4 mM EDTPA, 0.05→1.0 M NaCl pH at 5.5; Flow rate: 2.0 ml/min; Temperature: 30° C.; and Detection: 280 nm. The Mab peak shape does not degrade over a five-fold injection of Mab indicating good loadability of the column.

VI. Model Separations of Mab Contaminated with Albumin Protein

Figure 10:
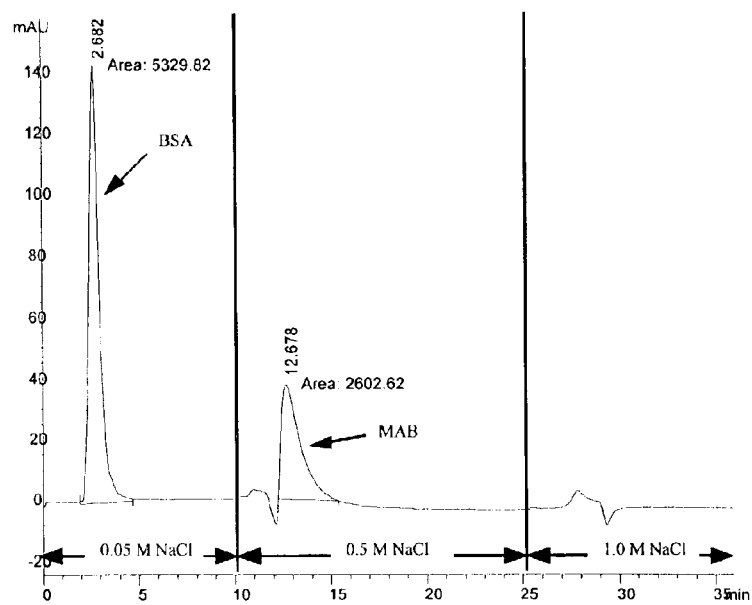
FIG. 10 is an exemplary plot of a 100 microliter injection of BSA (6.0 mg/ml) contaminated $IgG_{2a}$ (1.0 mg/ml) eluted by salt step gradient.

To demonstrate the ability of the EDTPA-modified zirconia particles to separate Mab from proteins, a pure Mab sample (1.0 mg/ml) (Sigma) was intentionally contaminated with a large amount of bovine serum albumin (BSA, 6.0 mg/ml). FIG. 9 shows a chromatogram resulting from a 100 µl injection of the BSA contaminated Mab. The BSA is unretained in the loading buffer and comes through in the fall-through fraction (0.05 M NaCl), while the Mab is retained until the mobile phase is switched to the eluting buffer, which contains 0.5 M NaCl. Additional 100 µl and 50 µl injections of the BSA contaminated Mab sample was run under identical conditions as those shown in FIG. 10. The condition for the injection is: Mobile phase: 20 mM MES, 4 mM EDTPA, 0.05→1.0 M NaCl pH=5.5; Flow rate: 2.0 ml/min; Temperature: 30° C.; and Detection: 280 nm. The ratioed area (peak area/injection volume) of the BSA and Mab peaks from the additional injections showed less than a 1% relative standard deviation.

VII. Isolation of Mab from Cell Culture Supernatant

Figure 11:
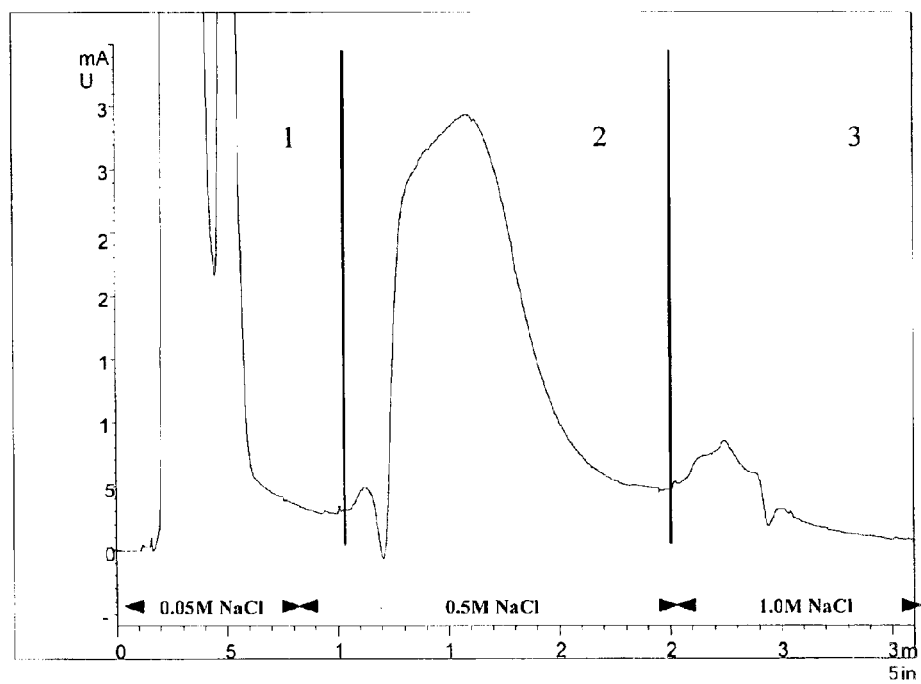
FIG. 11 is an exemplary plot of a 100 microliter injection of cell cultured supernatant eluted by salt step gradient.

FIG. 11 shows a typical chromatographic profile for the isolation of Mab from the cell culture supernatant. The condition for the isolation is: Mobile phase: 20 mM MES, 4 mM EDTPA, 0.05M→1.0 M NaCl pH=5.5; Flow rate: 2.0 ml/min; Temperature: 30° C.; and Detection: 280 nm. Unbound or very weakly retained proteins (serum albumin, etc.) passed through the column during the first five minutes. The UV trace at 280 nm returns to baseline after seven minutes (~14 column volumes) indicating near complete elution of contaminating protein.

A step change to 0.5 M NaCl was then made to elute bound Mab. A chromatographic peak at 280 nm indicates elution of bound protein that we identify as purified Mab. The Mab eluted between 16–25 column volumes. Finally, to elute any strongly bound proteins, a step increase to 1 M NaCl at fourteen minutes was employed. The column was flushed for six minutes or approximately twelve column volumes. A small peak is observed in the UV trace during this wash step. Interestingly, the same peak is also present in blank runs and is probably a system peak from the sudden (step) change in mobile phase composition. In order to restore the column for the next separation cycle, the column was then flushed with loading buffer (20 mM MES, 4 mM EDTPA, 50 mM NaCl at pH 5.5) for fifteen minutes prior to the next injection.

VIII. ELISA of Mab from Cell Culture Supernatant

Table 2 summarizes the Mab yield in the eluate fractions at various total protein and Mab challenges to the column.

TABLE 2

Summary of ELISA results

| | | Amount of Mab[a] (µgs) | | | | |
|---|---|---|---|---|---|---|
| | Feed[b] | Unretained (Fraction 1) | Eluate (Fraction 2) | Wash (Fraction 3) | % Yield[c] | % Overall Detected[d] |
| Run #1 | 588.9 | 18.41 | 564.16 | 5.61 | 95.8% | 99.9% |
| Run #2 | 605.4 | 18.32 | 544.06 | 4.89 | 89.9% | 93.7% |

[a]The amount of Mab in each fraction was estimated by ELISA.
[b]Cell culture supernatant was used as feed to the columns. Sample volumes of cell culture supernatant were lyophilized and reconstituted to give the desired Mab concentrations in feed. In each feed application the ratio of BSA to Mab remained relatively constant at 3.5:1.
[c]The % yield of the Mab was determined as a ratio of the total Mab in the eluate fraction (Fraction #2) to the total Mab present in the feed.
[d]The % overall detected amount of the Mab as determined by the ratio of the total Mab in the eluate fraction (Fraction #2) plus the Mab in fraction 1 and 3 to the total Mab present in the feed.

Chromatographic profiles were similar to the ones described above. The Mab concentration in different chromatographic fractions in each individual run was estimated by the ELISA protocol described in the phase I methods section. The percent yield of Mab in the eluate fraction was determined as a ratio of the total bio-active Mab in the eluate fraction to the total bio-active Mab injected. In most cases, yields of 92–98% were obtained with little or no detectable Mab in unretained or (column fall through) wash fractions. This yield is very high and represents a major breakthrough in a one-step method for the purification of Mab with a semi-preparative zirconia-based column. We also point out that serum albumin, the major protein of the cell culture, is unretained and thus does not consume any of the column's binding capacity.

IX. Gel Electrophoresis

Figure 12:
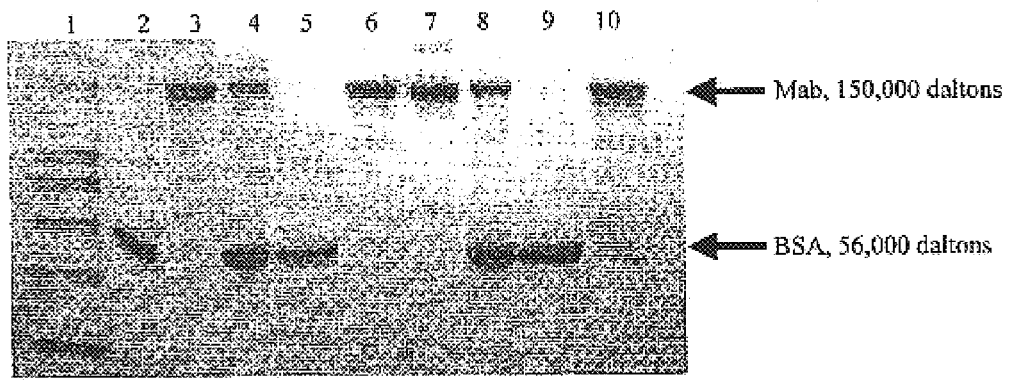
FIG. 12 is an exemplary gel electropherogram of collected fractions.

FIG. 12 shows a silver-stained, SDS-PAGE gel (8–16% gradient) electrophoresis purified fractions from a typical chromatographic separation. Chromatographic fractions from Run #1 and Run #2 (see Table 2) were selected for electrophoretic analysis. Lane 1 shows a molecular weight ladder. Lanes 2 shows a 3 µgs application of pure BSA. Lanes 3 and 7 show application of pure BSA and Mab at a total protein level of 2 µgs, respectively. Lanes 4 and 8 show an application of cell culture supernatant at a total protein level of 4 µgs. The cell culture supernatant has two distinct protein bands corresponding to BSA with a molecular weight of 56 kDa and Mab (IgG) with a molecular weight of 150 KDa with some additional minor bands. Lane 5 shows the unretained fraction from Run #1 at a total protein level of 3 µgs. The fall through fraction gave a band around 56 kDa similar to the pure BSA in Lane 2. Lane 6 shows the elution fraction from Run #1 at a total protein level of 3 µgs. The eluate fraction gave a band around 150 kDa similar to the pure Mab in Lane 3. In addition to the major Mab band at 150 kDa, a minor band at 56 kDa accounting for less than 2% of the area obtained by digital image processing was observed. Lane 9 shows the unretained fraction from Run #2 at a total protein level of 3 µgs. The fall through fraction gave a band around 56 kDa that is similar to the pure BSA in Lane 2. Lane 10 shows the elution fraction from Run #2 at a total protein level of 3 µgs. The eluted fraction gave a band around 150 kDa that is similar to the pure Mab in Lane 3. The purity of the Mab in the eluate fraction (Lanes 6 and 10) is estimated to be greater than 96% by digital image processing. Similar electrophoretic patterns were obtained with the fractions from other runs listed in Table 2 (data not shown).

X. Demonstrate Cleanability of Preparative EDTPA-modified Zirconia Columns

Figure 13:
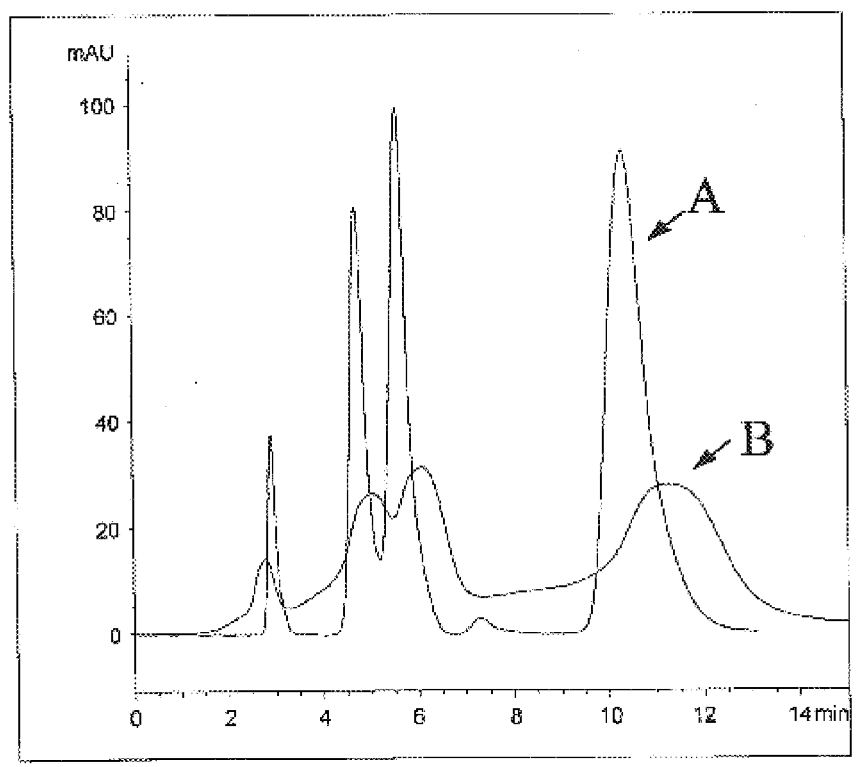
FIG. 13 is an exemplary plot of (A) separation of 2-hydroxypyridine, 2-ethylpyridine, 4-dimethylaminopyridine and 2,6-diaminapyridine on semi-prep column before fouling, and (B) separation of the same pyridine solutes after fouling column.

The semi-preparative column that was used for the Mab separations was deliberately fouled to demonstrate column cleanability. The column was fouled by manually injecting 200 µl BSA (250 mg/ml) into the column followed by 100 µl glutaraldehyde to cross-link the albumin. The efficiency of the column was then tested by separating four pyridine derivatives in a PEZ buffer containing 20 mM MES, 4 mM EDTPA, 5 mM NaCl, at pH 5.5. The separation after fouling the column was compared to the first separation of the pyridine derivatives in FIG. 13. The conditions for the separation are: Mobile phase: 20 mM MES, mM, EDTPA, 5 mM NaCl, pH=5.5; Flow rate: 2.5 ml/min; Temperature: 30° C.; and Detection: 254 nm. The separation of the pyridine derivatives is much less efficient after the column was contaminated with BSA and cross-linked glutaraldehyde.

In order to clean the column, the packing material was unpacked and collected in a sintered-glass funnel. The contaminated EDTPA-modified zirconia particles were washed consecutively with 200 mls water and 200 mls ethanol. There were large brown clumps of particles present in the particles from "fouling" the column. These particles were then dried on the funnel via vacuum and were placed in an forced air oven where they were burned for 4 hours at 400° C. The particles were then transferred to the programmable furnace and were heated for an additional 3 hours at 750° C. After this final heating step, the particles were completely white in color. Next the particles were re-screened with both the 25 and 38 micron sieves any. Out of the 25 grams used to initially pack the 15×1 cm semi-preparative column, 23.5 (94% recovery) grams were recovered. A new semi-preparative column was dry packed with the burned zirconia particles by adding 1.5 grams of the initial batch of EDTPA-modified zirconia particles.

Figure 14:
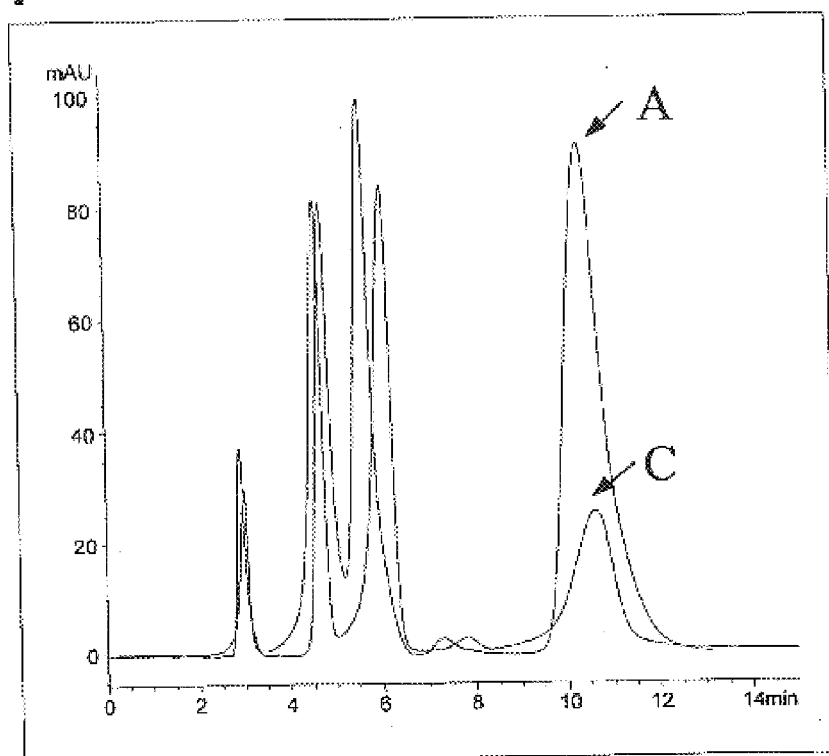
FIG. 14 is an exemplary plot of (A) separation of pyridine solutes, and (C) separation of same pyridine solutes after regenerating column.

The recovered zirconia column was then dynamically re-modified with EDTPA by flushing a 4 mM solution of EDTPA through the column for 64 hours at 0.5 ml/min and 50° C. After regenerating the zirconia particles with EDTPA, the pyridine derivatives were chromatographed again to see if the column regeneration was successful. As shown in FIG. 14, the retention of the pyridine probe solutes (C) is almost identical to those of the initial injection of the same solutes (A). The conditions for the separation are: Mobile phase: 20 mM MES, mM EDTPA, 5 mM NaCl, pH=5.5. Flow rate: 2.5 ml/min. Temperature: 30° C. Detection: 254 nm. There is a slight difference of peak heights since a new probe solute sample was made for the second injection. This result indicates that the particles were successfully re-modified with EDTPA. This demonstration shows how incredibly stable the porous preparative zirconia particles are. There is no other currently available stationary phase for Mab purification that can be regenerated in this manner.

XI. Purification of Mab Versus New Zirconia-Based Media

Porous preparative zirconia particles with an average diameter of 15–30 microns are coated with an organophosphate (EDTPA) to produce a bio-compatible stationary phase for the purification of proteins. The coated zirconia particles can be packed into preparative liquid chromatographic columns and used for rapid large-scale purification of monoclonal antibodies. These zirconia-based columns can be run at very high mobile phase linear velocities compared to the mechanically soft affinity gels such as Protein A and Protein G, which results in a dramatic increase in purification throughput.

EDTPA Modified zirconia can be used for the one-step purification of Mab. We have also shown that the final purified Mabs are as pure and as bioactive as those purified with current state of the art purification technologies based on Protein G and Protein A affinity chromatography.

XII. Scanning Electron Micrography of EDTPA Modified Preparative Zirconia

Figure 15:
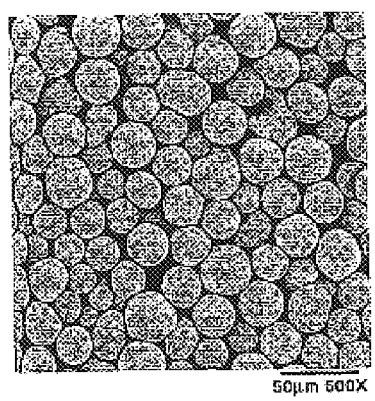
FIG. 15 is an exemplary SEM of preparative EDPTA modified porous zirconia.

FIG. 15 shows an SEM picture of preparative EDTPA modified porous zirconia particles. Nitrogen porosimetry studies show that this material has an average porous size of 300 Angstroms, a pore volume of 0.1 ml/gram and a surface area of 14 square meters per gram. These physical characteristics can be changed by the thermal treatment that the particles undergo during manufacture. Sintering at higher temperatures leads to lower surface area, but larger average pore size materials, while the inverse is also true.

XIII. Preparative Purification of Mab from Cell Culture Supernatant

Figure 16:
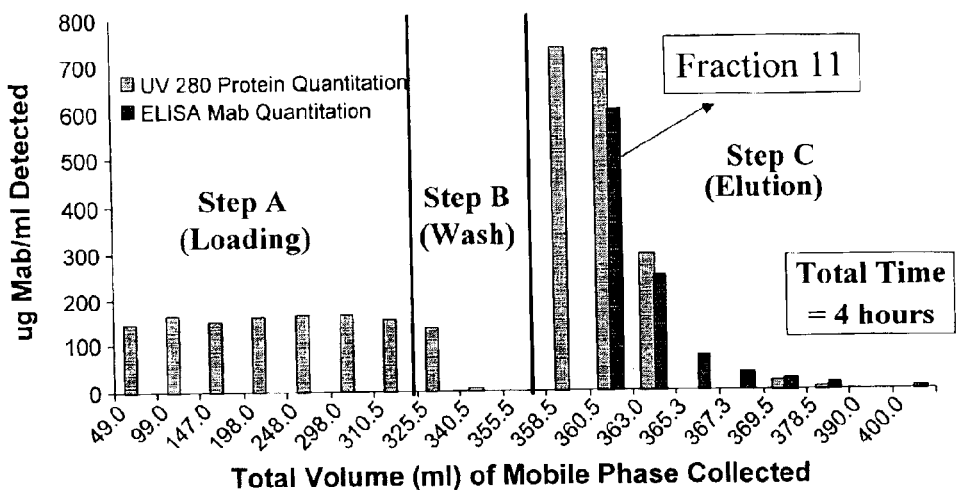
FIG. 16 is an exemplary graph of micrograms Mab per ml detected versus total volume (ml) of mobile phase collected.

One-step purification of Mab derived from mammalian hybridoma cell culture supernatant can be purified in a single chromatographic step using a simple three step elution on preparative EDTPA modified porous zirconia. FIG. 16 shows both the UV adsorbance and ELISA Mab quantitation of fractions that were collected during the loading, wash and elution steps of the purification process. The conditions for the experiment are: Step A=20 mM MES buffer, 4 mM EDTPA, 50 mM NaCl @ pH 4.0; Step B=20 mM MES buffer, 4 mM EDTPA, 50 mM NaCl @ pH 4.0, Step C=20 mM MES buffer, 4 mM EDTPA, 2.0 M NaCl @ pH 4.0. Flow Rate=1.6 mL/min, Injection size=31.6 mL serum-free cell culture supernatant diluted 10-times with loading buffer, (3.98 mg of Mab), Amount of preparative EDTPA modified porous zirconia in tube=10 grams. There was no detectable Mab in the loading and wash steps. The final purified Mab was virtually fully (100%) recovered as indicated by ELISA assay, whereas the recovery on Protein G is typically only 70% for this particular Mab variant.

Figure 17:
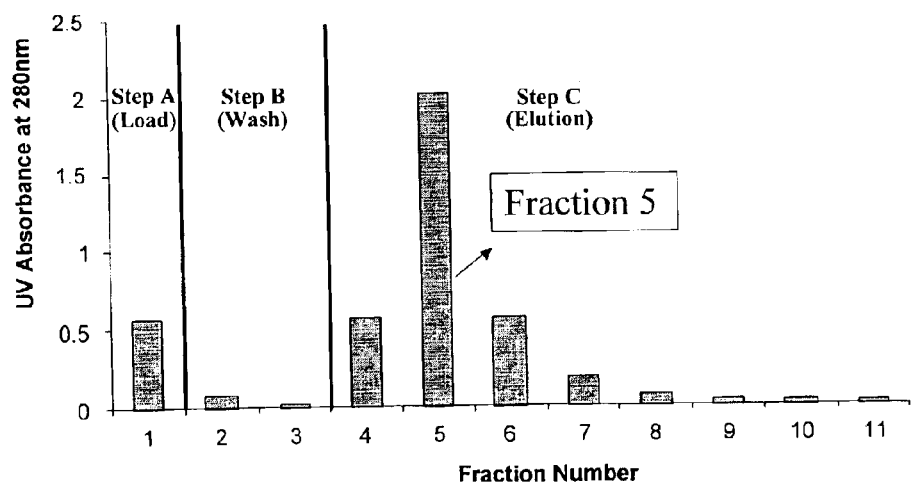
FIG. 17 is an exemplary graph of UV absorbance at 280 nm versus fraction number.

The Mab purified in the above run (FIG. 16) was then compared with Mab that we purified with Protein G affinity gel media. This was done by making an ELISA plate that can be used for diagnostic testing of target protein. The same amount of Mab is loaded onto an ELISA plate and then the same amount of target protein is placed on the plate and the test is "developed" by adding the second UV active Mab and the response is measured by UV adsorbance. This test was done by R&D systems on a Mab sample that they sell as a diagnostic ELISA kit. The comparative results between fractions 11–13 versus Mab purified by Protein G are shown in FIG. 17, which shows that the Mab purified on preparative EDTPA modified porous zirconia yielded more than 137% of the signal obtained on Protein G purified Mab. Furthermore, the level (for a blank test) was lower on the Mab purified on preparative EDTPA modified porous zirconia than on the Protein G purified Mab.

XIV. Fast Mab Purifications Using Preparative EDTPA Modified Porous Zirconia

TABLE 3

Fast Mab Purifications Using Preparative EDTPA Modified Porous Zirconia

| | | OD 280 Signal Versus Protein G Purified Mab | | |
|---|---|---|---|---|
| Protein Offered | Purified 28401.11 | Fraction 11 % of Purified | Fraction 12 % of Purified | Fraction 13 % of Purified |
| 15.625 | 0.037 | 139.2% | 139.1% | 140.6% |
| 31.25 | 0.0735 | 134.7% | 147.7% | 147.7% |
| 62.5 | 0.1365 | 143.2% | 146.8% | 147.2% |
| 125 | 0.2655 | 135.6% | 138.5% | 134.5% |
| 250 | 0.468 | 142.3% | 131.1% | 130.2% |
| 500 | 0.855 | 140.9% | 129.7% | 121.5% |
| 1000 | 1.5445 | 125.7% | 125.7% | 121.8% |
| | | 137.4% | 138.8% | 137.0% |

| Purified NSB | Fraction 11 NSB | Purified NSB | Fraction 12 NSB | Fraction 13 NSB |
|---|---|---|---|---|
| 0.056 | 0.043 | 0.060 | 0.052 | 0.042 |

Purifications performed with Protein G or Protein A affinity gels are very laborious and time consuming primarily due to compressibility of the substrate particle (Sephadex, a polysaccharide). These affinity gels cannot withstand any pressure and therefore are mostly used in gravity mobile phase feed conditions. On the other hand the same purifications performed on EDTPA-zirconia are very fast since the zirconia-based particles are mechanically stable and can be operated at much higher linear flow velocities and at higher pressure drops across the columns. The same Mab as was purified in FIG. 16 was purified under higher flow conditions. This purification required more than 24 hours on Protein G media (at R&D Systems), but was reduced to only 15 minutes (see FIG. 17) on preparative EDTPA modified porous zirconia. The conditions for the experiment of FIG. 17 are: Step A=20 mM MES buffer, 4 mM EDTPA, 50 mM NaCl @ pH 4.0; Step B=20 mM MES buffer, 4 mM EDTPA, 50 mM NaCl @ pH 4.0; Step C=20 mM MES buffer, 4 mM EDTPA, 2.0 M NaCl @ pH 4.0. Flow rate=60 mL/min, Injection size=31.6 mL serum-free cell culture supernatant diluted 4-times with loading buffer, (3.98 mg of Mab), Amount of EDTPA modified zirconia in tube=10 grams. The final purified Mab was virtually fully (100%) recovered as indicated by ELISA assay, whereas the recovery on Protein G is typically only 70% for this particular Mab variant.

The Mab purified in the above run (FIG. 17) was again compared with Mab that we purified with Protein G affinity gel media. This was done by making an ELISA plate that can be used for diagnostic testing of target protein (as described above). The comparative results between fractions 11–13 versus Mab purified by Protein G are shown in data Table 4, which shows that the Mab purified on preparative EDTPA modified porous zirconia yielded more than 108% of the signal obtained on Protein G purified Mab. Furthermore, Table 5 shows that the background signal (blank test) was slightly lower on the Mab purified on preparative EDTPA modified porous zirconia than on the Protein G purified Mab.

TABLE 4

Comparison of Mab Purification from Cell Supernatant on EDTPA modified porous zirconia and Protein G.

| | OD 280 nm | | |
|---|---|---|---|
| Protein Offered | Protein G Purified IgG | EDTPA-Zirconia Fraction 5 | EDTPA-Zirconia Fraction 5 |
| 15.6 | 0.0531 | 0.0502 | 94.5% |
| 31.3 | 0.0946 | 0.0992 | 104.9% |
| 62.5 | 0.1676 | 0.1892 | 112.9% |
| 125 | 0.3176 | 0.3632 | 114.4% |
| 250 | 0.5596 | 0.6362 | 113.7% |
| 500 | 1.0166 | 1.1507 | 113.2% |
| 1000 | 1.8151 | 1.8632 | 102.6% |
| | | Average % | 108.0% |

TABLE 5

| Background Signal | |
|---|---|
| Protein G Purified | EDTPA-zirconia Fraction 5 |
| NSB 0.055 | NSB 0.054 |

NSB = Non-Specific Binding, or Background

Figure 18:
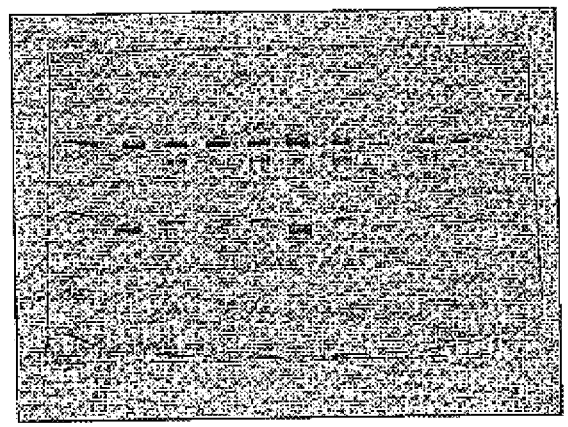
FIG. 18 is an exemplary silver-stained, SDS-PAGE gel comparing $IgG_1$ purified by Protein G (row 1 from right) and Rhinophase® AB (row 3 from right)

The purity of the Mab was determined to be equivalent to that obtained on the Protein G media. FIG. 18 shows an electrophoretic gel of $IgG_1$ purified on both Protein G and EDTPA modified zirconia media. The conditions for the experiment of FIG. 18 are: Electrophoresis was run under reducing conditions. Sample loading at 1 ug per lane. All other lanes are standards. The electrophoretic gel was run under reducing conditions so the purified $IgG_1$ shows two bands corresponding to the light (bottom band) and heavy (top band) chains of the Mab. This demonstration represents a roughly 100-fold improvement in purification time with an equivalent purity and higher recovery.

XV. Binding of Different Subclasses of IGs

Figure 19:
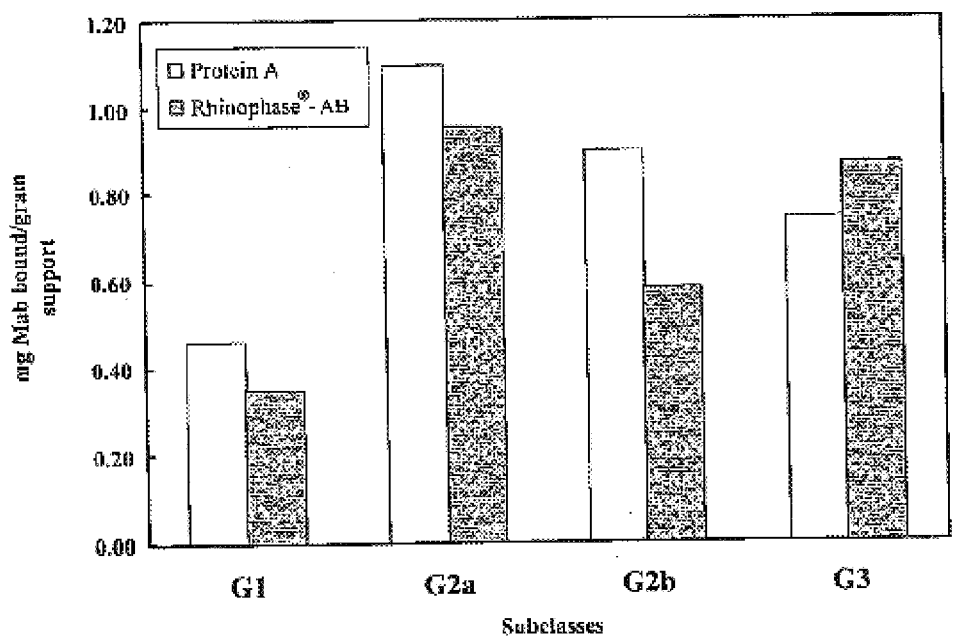
FIG. 19 is an exemplary graph of the binding capacity of EDPTA modified porous zirconia for a variety of different Mab subclasses.

EDTPA modified Zirconia can be used for the purification of different subclasses of IgGs as shown in FIG. 19 where the same amount of Mab was injected on both a Protein A column and onto a column packed with preparative EDTPA modified porous zirconia. The zirconia-based column had very similar binding affinity to Protein A media for these subclasses of Mab tested. The binding of pure Mab subspecies was studied in a batch experiment. The ratio of the amount of Mab bound to the beads to the amount of Mab fed taken as a percentage was defined as the "binding efficiency". Binding efficiencies in the range of 80–100% were obtained with subspecies $IgG_{2a}$, $IgG_{2b}$ and $IgG_3$. Binding efficiencies in the range of 50–80% were obtained with subspecies $IgG_1$.

Figure 20:
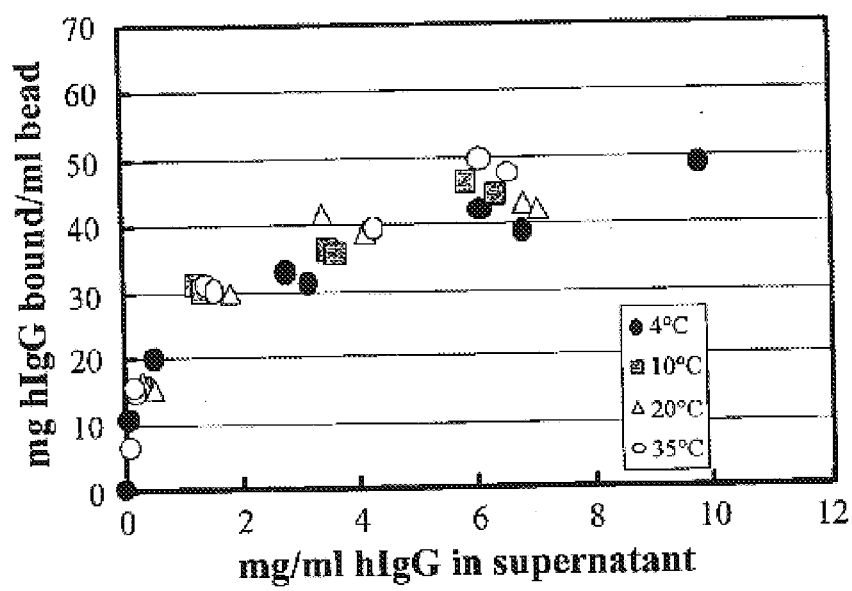
FIG. 20 is an exemplary plot of the effect of temperature on biding polyclonal human IgG on EDPTA modified porous zirconia.

XVI. Effect of Temperature on Binding of Polyclonal Human IgG EDTPA Modified Porous Zirconia FIG. 20 shows the temperature dependence on of binding affinity of polyclonal human IgG on EDTPA modified porous zirconia. As shown in the figure there is no decrease in binding of this polyclonal antibody on the EDTPA modified porous zirconia from 4 to 35° C.

EDTPA modified porous zirconia can also be used to purify different sub-classes of IgG and as well as IgA and IgM.

XVII. Binding Capacity of Different Classes of Immunoglobulins on EDTPA Modified Porous Zirconia Table 6 shows the binding capacity of different classes of pure immunoglobulins (Ig:IgG, IgA and IgM) by batch experiment on preparative EDTPA modified porous zirconia. The binding efficiencies were between 80–100% for IgG, and IgA and between 25–50% for IgM.

TABLE 6

| Sample | Capacity (mg antibody/ml particles)* |
|---|---|
| hIgG | 28 |
| hIgA | 9 |
| hIgM | 2 |

XVIII. Binding Capacity of IgGs from Different Animal Sources on Preparative EDTPA Modified Porous Zirconia The preparative EDTPA modified porous zirconia was found to bind pure pig IgG, human IgG and bovine IgG. Static binding capacities in the range of 25–35 mg IgG per ml of beads were obtained. Table 7 shows the amount of immunoglobulin adsorbed versus the amount offered to the preparative EDTPA modified porous zirconia.

TABLE 7

| Sample | Offered mg/ml beads* | Bound mg/ml beads* |
|---|---|---|
| Porcine IgG | 37 | 28 |
| | 18 | 11 |
| | 9 | 8 |
| | 5 | 4 |
| | 1 | 1 |
| Bovine IgG | 22 | 19 |
| | 11 | 10 |
| | 6 | 5 |
| | 3 | 3 |
| | 1 | 1 |
| Human IgG | 22 | 19 |
| | 11 | 11 |
| | 6 | 5 |
| | 3 | 3 |
| | 1 | 1 |

XIX. Packing of Preparative EDTPA Modified Porous Zirconia into Preparative Liquid Chromatographic Columns A major operational advantage to preparative EDTPA modified porous zirconia over other soft affinity gels is that it can be packed into large liquid chromatographic columns and run under high flow and high-pressure conditions. The preparative column was packed by pouring dry material into the column while tapping the column and then allowing the particles to settle. Isopropanol was then pumped through the column at 30 mL/min for 5 minutes. The inlet end fitting was then removed and the column was then "topped off" with more material. This process was repeated 3 more times until there was no void development at the head of the column. A picture of the resulting column is shown in FIG. 21.

Figure 21:
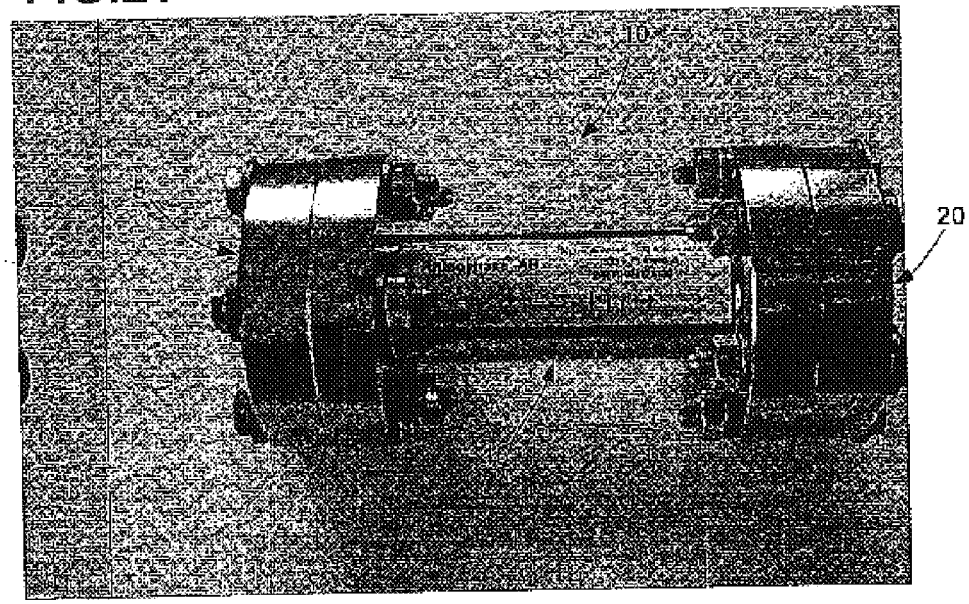
FIG. 21 is a photographic representation of an exemplary liquid chromatographic column.

The column of FIG. 21 can be used for separation and/or purification processes. An aqueous solution containing a mobile phase and a sample can be passed into a first end 5 of the column 10 into a body 15 of the column 10 and passed out of or discharged from a second opposite end 20 of the column 10 as an eluent. The eluent can be analyzed and/or collected after passing out the second opposite end 20. A modified metal oxide, as described herein, can be packed within the liquid chromatographic column 10 for separation and/or purification processes of immunoproteins.

Figure 22:
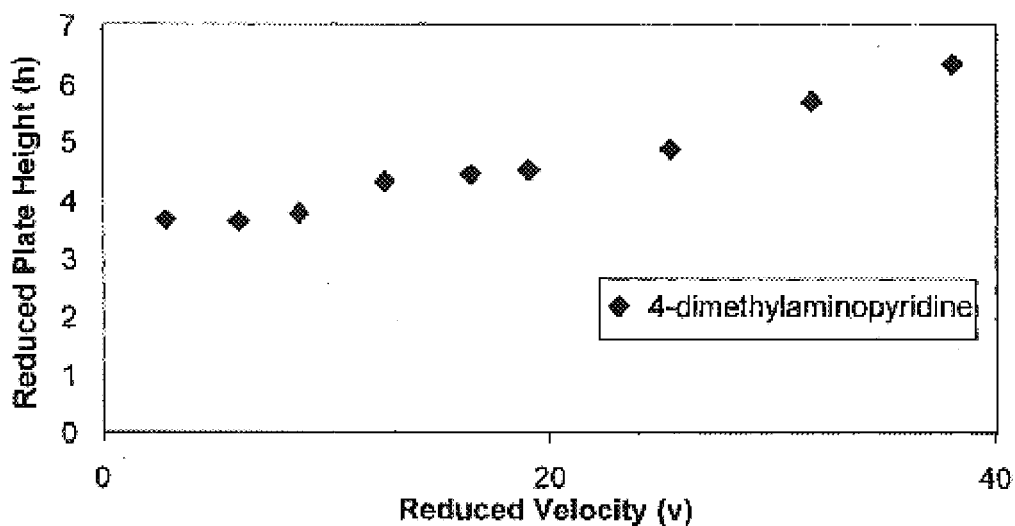
FIG. 22 is an exemplary graph of a flow study on a 100×25.4 mm preparative EDTPA modified porous zirconia column.

XX. Flow Study on a Preparative Column Packed with EDTPA Modified Porous Zirconia The column shown in FIG. 21 was used to perform a flow study on preparative EDTPA modified porous zirconia, which shows that for a small solute such as 4-dimethylaminopyridine that high flow rates do not decrease the efficiency of the column significantly, as shown in FIG. 22. This weak dependence of column efficiency with flow velocity means that purifications can be run at higher flow rates without significantly decreasing the column's chromatographic performance. The mobile phase used for the study was 20 mM MES, 5 mM NaCl, 4 mM EDTPA at pH=5.5. The test solute used was 4-dimethylaminopyridine (1.0 mg/ml) spiked w/acetone.

XXI. Synthesis of Porous Titania Particles

A. Synthesis of Titania Colloids

Based on the reference, *Anal. Chem.* 73,686–688 (2001), 120 g of ice was added to a 1000-mL round-bottom flask. Under conditions of an ice bath and mechanical stirring, 40 ml of titanium tetrachloride was added drop by drop. The hydrolysate was dissolved in cold water, after which titanium oxychloride sol was obtained as a starting material. 200 g of water and 4 mL of acetylacetone were added successively. The pH of the solution was adjusted to 0.36 using 1 mol/L sodium hydroxide during 2 hours, and then the solution was stayed at room temperature for at least 72 hours. The sol was made to 900 mL total volume using water.

B. Synthesis of Titania Particles 21.6 g of urea was added. After the urea was dissolved, 21.2 mL of 38% formaldehyde solution was added at approximately 15° C. and, the solution was mixed well. After 5 h of reaction, the mixture was diluted to about 400 mL with water and stirred for a few minutes. The aggregated particles were then separated by filtration and subjected to a series of washing processes using water and acetone.

The particles were transferred to a crucible with a spatula and were dried in a vacuum oven at 120° C. for three hours. The crucible was then transferred to a combustion oven, the temperature was ramped at 5° C./min to 400° C., and the particle were kept at 400° C. for three hours to burn off any remaining carbon. Then the temperature was raised to 600° C. at 5° C./min and held at 600° C. for five hours to completely remove all carbon and to allow densification. Finally, the temperature was decreased at 5° C./min to room temperature.

XXII. Mab Retention of EDTPA Modified Zirconia, Titania and Alumina

Due to the similar Lewis acidity of the surfaces of metal oxides (such as alumia, titania, zirconia and hafnia) we wanted to test these metal oxides for their ability to adsorb EDTPA and be used for Mab purification. The zirconia sample was made by spray drying as previously described. The titania sample was made by the PICA process (ZirChrom patented process for zirconia) and the alumina was purchased from Selecto Scientific (Ga., Atlanta). Both the zirconia and titania particles were spherical and the alumina was irregular shaped. Table 8 shows the physical characteristics of the metal oxides that were used for this study:

TABLE 8

Physical characteristics metal oxides

| Substrate | Average Particle Size Range (microns) | Surface Area ($m^2/g$) | Pore Volume (mL/g) | Average Pore Diameter (Å) |
|---|---|---|---|---|
| Zirconia | 3 | | | |
| Titania | 4–6 | 38 | — | 300 |
| Alumina | 90–200 | 300 | 0.55 | 73 |

Figure 23:
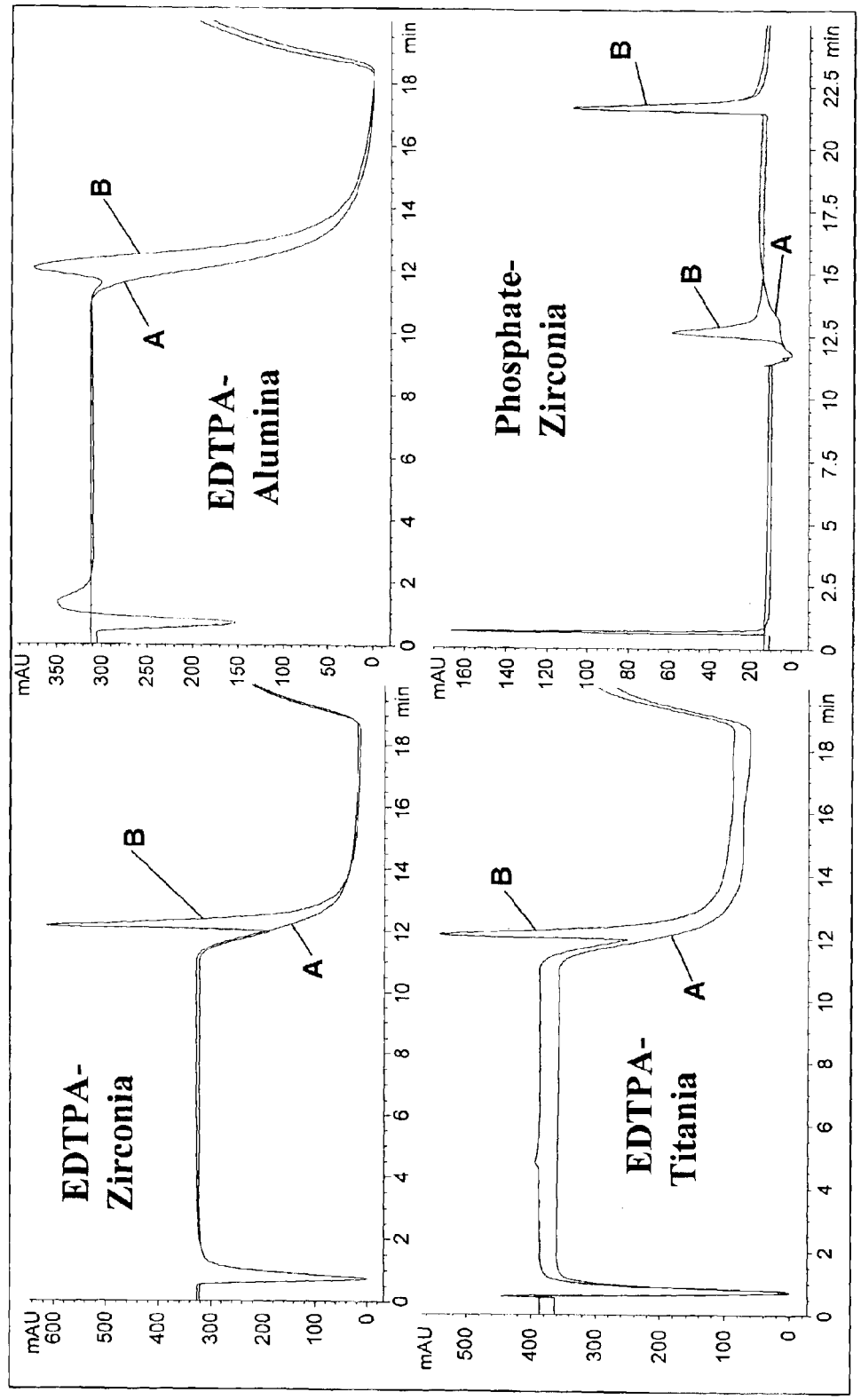
FIG. 23 are exemplary plots of chromatography of Mab on EDPTA modified zirconia, alumina and titania.

Three columns were packed into an HPLC column with the above zirconia, titania and alumina particles and then each material was modified with EDTPA, except for the phosphate modified zirconia, using the following procedure:

1. Pack three 30×2.1 mm id. HPLC columns.
2. Pump a solution containing 0.2 molar EDTPA at pH 2.5 through the column at a flow rate of 0.052 mL/min with a column temperature of 100° C.
3. Use the following chromatographic conditions for model purification of pre-purified $IgG_1$: LC Conditions: Mobile phase, 100% A stepped to 100% B at 7 minutes, returning to 100% A at 15 minutes, where A is 4 mM EDTPA, 20 mM MES, 50 mM NaCl, pH 4.0, and B is 4 mM EDTPA, 20 mM MES, 2.0M NaCl, pH 4.0; Temperature, 30° C.; Detection at 280 nm; Injection volume, 50 µL;
   Antibody=Ms×hPARC, clone # 64509.11 from R&D Systems; Sample concentration=1 mg/ml The phosphate modified zirconia was produced by taking a bare zirconia column and then running a mobile phase comprised of 20 mM Ammonium fluoride, 20 mM MES, 50 mM NaCl, pH 4.0 for 3 hours at 1.0 ml/min. and 30° C. through the column. In order to first test the ability of different EDTPA modified metal oxides to purify Mab a model solution of pure Mab was injected on the different columns to see if the Mab would be retained and then elute under the same conditions that are effective on EDTPA modified zirconia. FIG. 23 shows a blank run (A) and a Mab injection (B) on each column. The loading, wash and elution steps are the same mobile phases as used in FIG. 16. The chromatographic runs were all performed on an Agilent 1100 HPLC equipped with variable wavelength UV detector and connected to a ChemStation for data collection. The conditions for the experiment of FIG. 23 are: Column Dimension, 30×2.1; Mobile phase, 100% A stepped to 100% B at 7 minutes, returning to 100% A at 15 minutes, where A is 4 mM EDTPA, 20 mM MES, 50 mM NaCl, pH 4.0, and B is 4 mM EDTPA, 20 mM MES, 2.0M NaCl, pH 4.0; Temperature, 30° C.; Detection at 280 nm; Injection volume, 50 mL; Antibody=Ms×hPARC, clone # 64509.11 from R&D Systems; and Sample concentration 1 mg/ml. EDTPA modified zirconia, alumina and titania as well as inorganic phosphated modified zirconia all retained the Mab sample during the loading step and released the Mab during the elution step of the run. The all of these different types of metal oxides can be loaded with EDTPA and used for antibody purifications. Furthermore, as discussed in U.S. Pat. No. 5,141,634, inorganic phosphate modified zirconia is also useful for Mab purifications.

Table 9 shows the ELISA results of four different fractions collected on the different metal oxides studied. EDTPA modified zirconia had the highest recovery of the Mab injected, followed by phosphate modified zirconia, EDTPA modified titania and EDTPA modified alumina, respectively.

TABLE 9

ELISA of Elution Fractions for Different Metal Oxides

| Fraction Time (min.) | Total Detected Mab (mg) by ELISA | | | |
|---|---|---|---|---|
| | EDTPA-Zirconia | EDTPA-Titania | EDTPA-Alumina | Phosphate-Zirconia |
| 5 | 0 | 0 | 5.3 | 0 |
| 10 | 0 | 0 | 0 | 0 |
| 15 | 14.3 | 12.9 | 7.2 | 12.7 |
| 20 | 0 | 0 | 0 | 0 |

XXIII. Purification of Mab from Cell Culture Supernatant on 100 Micron Oil-Emulsion EDTPA Modified Zirconia 100 micron porous zirconia made by an oil-emulsion technique (previously discussed in zirconia patents) were used to purify Mab derived from cell culture supernatant in a single step purification. It was possible to just use gravity feed of the mobile phase since the particles used were so large. The method used to do the purification is described below.

A. Oil Emulsion Procedure

A 5 gallon reaction chamber (pail) is placed in a 20 mL Cole-Parmer water bath using 2 quick-grip clamps to hold the chamber in the water bath. Planter's peanut oil (3600 mL), purchased from Cub Foods, and 65% Tech Grade Oleyl alcohol (3600 mL), purchased from Aldrich, is then added to the reaction chamber. A Catramo Stirrer w/a bow-tie stir bar is then situated next to the water bath so the stir bar is in the oil/alcohol mix. The water bath is then brought to 93° C. (oil/alcohol mixture measured at 93.7° C.) while the reaction mixture is stirred at 100 rmp w/the bow-tie stir bar. Zirconia colloid, Zr 100/20 90% large, (1200 mL), purchased from Nyacol Nano Technologies Inc., is then added to the reaction chamber using a Masterflex pump set at 500 mL/minute. As the colloidal zirconia is added the stir rate is increased to 375 rpm. The resulting mixture of oil/alcohol/zirconia is then stirred at 375 rpm while heated at 93° C. for 6 hours. After the 6 hours of stirring with heat, the water bath is turned off and the stirring stopped. The reaction mixture is allowed to cool and settle overnight. The following morning, the supernate can be decanted away from the resulting particles. The particles are washed with approximately 500 mL of ethanol onto a 0.45 um membrane filter. The particles are then dried by vacuum on the filter. Additional drying is done by placing the particles in a dish in the vacuum oven and pulling air through the oven (vacuum on and by-pass opened partially) while heating at 100° C. After drying, the particles are transferred to the forced air oven for burning. The particles are burned for 2.5 hours at 800° F. Once burned, the particles are transferred to crucibles and placed in a programmable furnace for sintering. The particles are sintered at 750° C. for 6 hours and then 900° C. for 3 hours with 40° C./minute ramping.

Once the material have been dried, burned, and sintered, the resulting particles are sized using shaker sieves. The sieves used have 38 um, 45 um, 63 um, and 90 um screens which results in fractions: less than 38 um, 38–45 um, 45–63 um, 63–90 um, and greater than 90 um. Table 10 breaks the yield of the fractions down for the procedure. After size classifying, the particles were treated to base and acid washes.

B. Oil Emulsion Particle Modification

Figure 24:
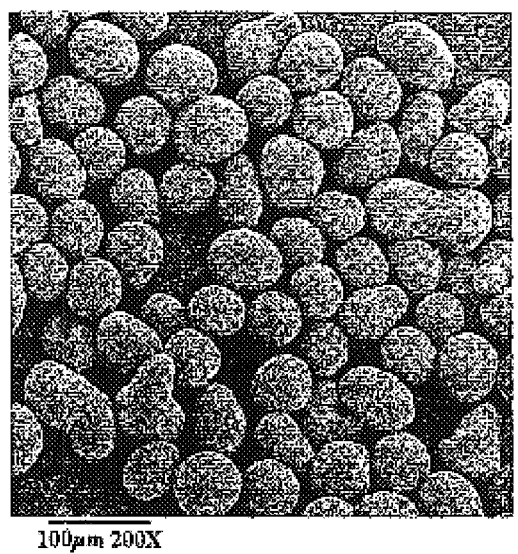
FIG. 24 is an exemplary SEM of oil emulsion zirconia particles.

Base and acid treated oil emulsion particles greater than 90 um (100 g) are placed in a 1 L two neck, round bottom flask with 500 mL of 0.2M N,N,N',N'-Ethylenediaminetetra (methylenephosphonic Acid) (EDTPA) pH=2.6, purchased from TCI America. (Solution made by dissolving crystalline EDTPA in water and adjusting pH with 50% NaOH and then filtering on a 0.45 um membrane.) The flask is then placed in a thermowell heating mantle with a condenser attached through the main (center) neck of the flask and a line bubbling air into the flask through the side (small) neck of the flask. The line with air is needed to reduce the bumping that occurs during the reflux. The air is bubbled into the flask at 25 mL/minute. The flask was heated at level 4 on the heating mantle and allowed to reflux for 4 hours. After refluxing, the heating mantle is turned off and the flask allowed to cool to the touch. The particles are then collected on a 0.45 um membrane filter. The now modified particles are rinsed twice with 200 mL of HPLC grade water (each wash) followed by 2 washes with 200 mL of HPLC grade Ethanol (each wash), purchase from Pharmco. The particles are dried overnight by pulling air through the particle cake on the filter. FIG. 24 shows a SEM of the resultant oil emulsion zirconia particles.

TABLE 10

Oil Emulson Particle BET

| Sample | SA (m^2/g) | Pore vol. (mL) | Pore Diameter (A) | Peak Max. (A) |
|---|---|---|---|---|
| <38 um | 21.0 | 0.224 | 427.9 | 600 |
| 38–45 um | 20.2 | 0.226 | 447.5 | 600 |
| 45–63 um | 20.7 | 0.235 | 454.1 | 550 |
| 63–90 um | 20.2 | 0.232 | 460.4 | 600 |
| >90 um | 21.9 | 0.239 | 436.4 | 550 |

C. Mab Purification on 100 Micron EDTPA Modified Oil Emulsion Porous Zirconia Particles A similar purification run was as described above in FIG. 16 was performed on 100 micron EDTPA modified oil emulsion porous zirconia. The samples purified was an $IgG_1$ (clone #28401.1 from R&D Systems) with a concentration in the cell culture supernatant of about 126 micrograms/mL. As before the purification was done in SPE Tubes by the following procedure: Put 10 g of O. E. slurried in 20 mL of Loading Buffer (20 mM MES, 50 mM NaCl, 4 mM EDTPA, pH=4.0) and sonicated for 5 seconds under vacuum followed by 2 minutes with vacuum and no sonication. Pour slurry into a 60 mL SPE tube fitted with a polyethylene frit and flow 150 mL of Loading Buffer through the bed.

Sample Loading: 31 mL of IgG1 clone 28401.1 was diluted to 125 mL with Loading Buffer. The sample was then loaded by gravity with a flow rate of ~30 mL/minute.

Elution: After loading, the IgG1 was eluted with Elution Buffer (20 mM MES, 2.0M NaCl, 4 mM EDTPA, pH=4.0). Eight fractions were then collected during the purification run. Fractions 6–8 were collected during the elution stage of the process and an ELISA plate was made from these fractions (as previously described in Table 4 and 5). As shown in Table 11, Fractions 6, 7 and 8 showed 62%, 107% and 107% of the signal obtained from Mab that was purified using Protein G purification media. These results are almost identical to the results obtained on the 25 micron zirconia used in Table 4 and 5. Furthermore, the background signal due to non-specific binding was only slightly lower for Fraction 6 and slightly higher for Fractions 7 and 8. It was thus determined that 100 micron EDTPA modified zirconia made by oil-emulsion can be used for one-step fast purification of Mab from cell culture supernatant.

TABLE 11

Elisa Analysis of Mab Elution Fractions Collected on 100 Micron EDTPA Modified Zirconia 284.01.111 Fractions Collected May 03, 2001
(Plates coated based on A280 Concentrations)

| | Purified IgG OD | Fraction 6 OD | Fraction 6% of Purified | Fraction 7 OD | Fraction 7% of Purified | Fraction 8 OD | Fraction 8% of Purified |
|---|---|---|---|---|---|---|---|
| 15.625 | 0.102 | 0.064 | 62.7% | 0.114 | 111.8% | 0.118 | 115.7% |
| 31.25 | 0.23 | 0.121 | 52.6% | 0.246 | 107.0% | 0.247 | 107.4% |
| 62.5 | 0.457 | 0.276 | 60.4% | 0.48 | 105.0% | 0.465 | 101.8% |
| 125 | 0.788 | 0.484 | 61.4% | 0.865 | 109.8% | 0.868 | 110.2% |
| 250 | 1.359 | 0.874 | 64.3% | 1.474 | 108.5% | 1.467 | 107.9% |
| 500 | 2.16 | 1.388 | 64.3% | 2.306 | 106.8% | 2.269 | 105.0% |
| 1000 | 2.883 | 2.017 | 70.0% | 2.842 | 98.6% | 2.92 | 101.3% |
| Average % | | | 62.2% | | 106.8% | | 107.0% |

| Purified | Fraction 6 | Fraction 7 | Fraction 8 |
|---|---|---|---|
| NSB | NSB | NSB | NSB |
| 0.16 | 0.146 | 0.194 | 0.191 |

NSB = Non-Specific Binding, or Background

ADDITIONAL EXAMPLES

Capacity of Human IgG on Modified Zirconia and Modified Titania

| | |
|---|---|
| Instrumentation: | Agilent 1100 LC Pump and UV Detector |
| | Waters U6K Manual Injector |
| Hardware: | Isolation Technologies UNICAP Guard Holder |
| | Catalog 9121-V |
| | Isolation Technologies 1 cm × 2 mm Drop in Guard Cartridge Assemblies with 0.5 micron frit caps |
| | Catalog 9103-05 |
| Antibody: | Sigma Human IgG-Reagent Grade From Serum, |
| | 100 mg |
| | Catalog I-4506, Lot 31K9001 |
| Chemicals: | Sigma 2-[N-Morpholino]ethanesulfonic acid Hydrate (MES), ≧99.5%, 250 g Catalog M-8250, Lot 29H5429 |
| | Sigma Sodium chloride (NaCl), 99 + % ACS Reagent, 500 g |
| | Catalog 22,351-4, Lot 12516HI |
| | TCI America N,N,N',N'-Ethylenediaminetetra(methylenephosphonic acid) (EDTPA), 93%, 5 kg |
| | Catalog E0393, Lot OGK01 |
| | Fisher Acetone, HPLC Grade, 4L |
| | Catalog A949-4, Lot 011010 |
| Samples: | Modified Zirconia 25 micron 300 Angstrom, Lot 16–140 |
| | Modified Zirconia 25 micron 500 Angstrom, Lot 39–139 |
| | Modified Titania 40 micron 300 Angstrom, Lot 22–128 |
| | Modified Titania 40 micron 500 Angstrom, Lot 22–126 |
| | Modified Titania 40 micron 1000 Angstrom, Lot 43–142 |
| | Modified Titania 40 micron 2000 Angstrom, Lot 22–129 |

Note:
All bare titania samples were acquired from Sachtleben Chemie GmbH in Duisburg, Germany. The zirconia particles were produced by ZirChrom Separations, Inc. in Anoka, Minnesota. All surface modification of the materials was done at ZirChrom Separations, Inc.

Sample Modification

All of the samples listed above were modified using the following procedure. A 0.2M EDTPA solution, pH 2.6, was made by dissolving 10.9 g of EDTPA in 125 mL of HPLC grade water. To reach the pH and aid in dissolution, a 50% NaOH solution was added to the 0.2M EDTPA solution with stirring and low heat. The EDTPA solution was then filtered on a 0.45 micron membrane filter prior to use. To a three-neck, 500 mL round bottom flask, 25 g of sample was added with the 125 mL of filtered 0.2M EDTPA solution made previously. The flask was then swirled to help get the sample into solution and the pores of the sample wet. The flask was then placed in a thermo well. A metal tube was placed through a stopper and into the middle neck of the flask. Air was run through the metal tube at 500 ml/min to keep the sample in solution and to avoid bumping. A condenser was placed in one of the side necks and a stopper was placed in the other side neck. The flask was heated at level 5 and allowed to reflux for 4 hours. After refluxing, the flask was allowed to cool to the touch. The airline was turned off and the water to the condenser was turned off. The contents of the flask were filtered on a 0.45 micron membrane filter. The sample was then washed two times with 200 mL of water each time. This was followed by 2 washes with 200 mL of ethanol each time. Air was pulled through the sample cake to dry the sample and than transferred to an appropriately labeled container.

Capacity Study

The Agilent 1100 0.17 mm×60 cm capillary tubing from the pump valve to the injection valve was removed at Port 1 from the injection valve. This tubing was run from the Agilent 1100 pump valve to the inlet on the Waters U6K Manual Injector. A¹⁄₁₆"OD×0.005"ID×16" piece of PEEK tubing was run from the Waters U6K Manual Injector to the UNICAP Holder. The holder was screwed directly to the Agilent 1100 UV Detector. Note: The sample loop on the Waters U6K Injector that was used was 2 mL.

Each of the samples listed above was packed in a 1 cm×2 mm guard cartridge as described above in hardware. To pack, 0.5 g of each sample was weighed into a 4 dram vial and slurried with 10 mL of HPLC grade Isopropanol (IPA). The vials were shaken vigorously prior to packing. (Sonication was not used for fear of breaking the titania particles.) The cartridges were packed at 2000 psi with an IPA push using a 5 mL bomb. Each cartridge was packed for 2 minutes.

Each packed cartridge was placed in a guard holder, which was integrated into the set-up as described in paragraph one of the description. The pump was run at 0.2 ml/min (Agilent 1100) with Loading Buffer (20 mM MES, 4 mM EDTPA, 50 mM NaCl, pH=4.0) to equilibrate the cartridge. The first runs for each material were done using a 3% v/v solution of Acetone in Loading Buffer to determine the dead time for the cartridge. This was done by injecting 2 mL of the 3% v/v solution in the Waters manual injector using a syringe while the injector was in the Load position. The Agilent 1100 autosampler was set to 0.0 mL and a run time of 20 minutes with the detector set at 254 nm. Using ChemStation, an injection was made using the aforementioned parameters. This allowed for data acquisition even though a manual injection was done using the Waters injector. When the Agilent 1100 autosampler injected, the valve on the Waters manual injector was switch from Load to Inject, which allowed flow through the previously loaded sample loop. Each Acetone run was done in duplicate to show agreement.

After the Acetone runs were completed, similar runs were done using the Human IgG described above. The IgG was reconstituted at 3.5 mg/ml in Loading Buffer. The flow rate throughout the capacity study remained at 0.2 ml/min. The cartridge was equilibrated in Loading Buffer and just as with Acetone, the sample loop was loaded using the 3.5 mg/ml Human IgG at a volume of 2 mL (7 mg total). Exactly the same run parameters were used with the Acetone injections with the exception of the detector wavelength which was changed to 280 nm for detection of the antibody. This portion of the experiment can be referred to as Loading and the purpose was to generate a Loading Curve. The eluent from each run was collected and appropriately labeled. At the end of the 20 minute run, the pump was turned off and the mobile phase switched to Elution Buffer (20 mM MES, 4 mM EDTPA, 2M NaCl, pH=4.0). This step was to elute the IgG from the cartridge. Using the same parameters as for Loading with the exception of replacing the Loading Buffer with Elution Buffer, another 20 minute run was done. As with the Loading, the eluent from the run was collected and appropriately label. After eluting the IgG, the column was re-equilibrated in Loading Buffer for the next Loading run. All of the runs were done in duplicate for each sample.

Results

Figure 25:
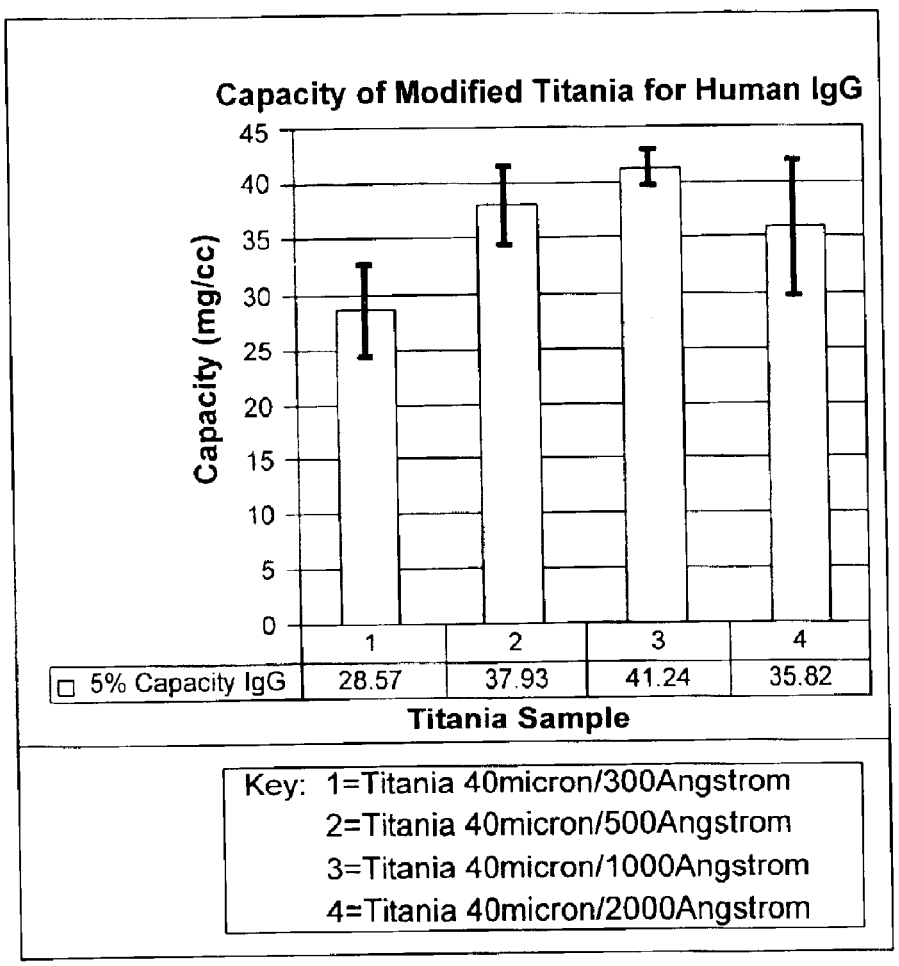
FIG. 25 is an exemplary plot of capacity of EDPTA modified titania for polyclonal human IgG.

By using the Loading Curves generated in the experiment, a capacity of the human IgG for the different modified zirconia and modified titania samples was determined at 5% saturation, as shown in FIG. 25. As that each run was performed in duplicate the values below is the average of the two runs. The charts contain the error bars for these values. The collected samples are being stored and can be tested by ELISA at some later time. Figure A shows the capacity for polyclonal human IgG on 25 micron zirconia with different average pore sizes. The average capacity for 500 angstrom zirconia was almost twice that of 300 angstrom zirconia. This is likely due to greater chromatographically accessible surface area to the large Mab molecule. Even though the surface area of the 300 angstrom material is larger, the Mab cannot interact with the greater surface area due to size exclusion. This result suggested that there is an optimal pore size that balances the tradeoff between overall surface area and pore size large enough to allow diffusion of antibodies into the porous particle. Figure B shows the same study done on four different EDTPA modified porous titania particles of different pore size. The Ab capacity goes through a maximum binding capacity at about 1000 angstrom pore size. At 2000 angstrom pore size the average capacity was lower than the 1000 angstrom average pore size material. For this reason we claim the following particle characteristics as optimal for antibody purifications: particles from 3–100 microns in average diameter with pores sizes ranging from 400 to 1500 angstroms and surface areas from 3–40 square meters per gram, and pore volumes from 0.1 to 0.4 mL/gram.

| | |
|---|---|
| Surface Area/ | Zirconia 300 Angstrom—13.7 $m^2/g$, 0.1 mL/g |
| Pore Volume: | Zirconia 500 Angstrom—4.9 $m^2/g$, 0.06 mL/g |
| Surface Area/ | Titania 300 Angstrom—15 $m^2/g$, 0.12 mL/g |
| Pore Volume: | Titania 2000 Angstrom—<5 $m^2/g$, 0.1 mL/g |

The present invention should not be considered limited to the particular examples or materials described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

We claim:

1. A chromatographic material comprising:

a porous metal oxide particle having a diameter of about 15 to 100 microns, a surface area of about 10 to 50 m.sup.2/g, and a pore size of about 200 to 600 Å; and a multi-Lewis base moiety incorporated onto the surface of the particle, wherein the multi-Lewis base moiety is an amount sufficient enough to impart cation-exchange characteristics to the particle for separations.

2. The chromatographic material of claim 1, wherein the porous metal oxide comprises a material selected from the group consisting of zirconia, titania, and alumina.

3. The chromatographic material of claim 1, wherein the multi-Lewis base moiety is a phosphate.

4. The chromatographic material of claim 3, wherein the phosphate comprises about 0.5 to 15% by weight of the chromatographic material.

5. The chromatographic material of claim 3, wherein the phosphate is derived from phosphoric acid.

6. The chromatographic material of claim 3, wherein the phosphate is an inorganic phosphate.

7. The chromatographic material of claim 1, wherein the multi-Lewis base moiety is ethylenediamine-N,N-tetra (methylenephosphonic acid).

8. The chromatographic material of claim 1, wherein the chromatographic material is substantially stable in an aqueous solution of a pH of about 1 to 14.

9. The chromatographic material of claim 1, wherein the porous metal oxide particle is a spherule.

* * * * *

UNITED STATES PATENT AND TRADEMARK OFFICE
CERTIFICATE OF CORRECTION

| | | |
|---|---|---|
| PATENT NO. | : 6,846,410 B2 | Page 1 of 1 |
| APPLICATION NO. | : 10/428231 | |
| DATED | : January 25, 2005 | |
| INVENTOR(S) | : Clayton V. McNeff et al. | |

It is certified that error appears in the above-identified patent and that said Letters Patent is hereby corrected as shown below:

After Col. 1, Line 7, please insert the following paragraph:

--GOVERNMENT FUNDING

This invention was made with government support under Grant No. 5R44GM58354-03, awarded by the U.S. Department of Health and Human Services. The Government has certain rights in the invention.--

Signed and Sealed this

Nineteenth Day of August, 2008

JON W. DUDAS
*Director of the United States Patent and Trademark Office*